(12) United States Patent
Cigan

(10) Patent No.: US 10,822,614 B2
(45) Date of Patent: *Nov. 3, 2020

(54) MANIPULATION OF DOMINANT MALE STERILITY

(71) Applicant: PIONEER HI-BRED INTERNATIONAL, INC., Johnston, IA (US)

(72) Inventor: Andrew Mark Cigan, Madison, WI (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/138,192

(22) Filed: Sep. 21, 2018

(65) Prior Publication Data

US 2019/0010513 A1    Jan. 10, 2019

Related U.S. Application Data

(63) Continuation of application No. 14/774,272, filed as application No. PCT/US2014/023932 on Mar. 12, 2014, now Pat. No. 10,113,181.

(60) Provisional application No. 61/788,950, filed on Mar. 15, 2013, provisional application No. 61/778,069, filed on Mar. 12, 2013.

(51) Int. Cl.
| | |
|---|---|
| *C12N 15/82* | (2006.01) |
| *C12N 15/29* | (2006.01) |
| *A01H 1/02* | (2006.01) |
| *A01H 6/46* | (2018.01) |
| *C07K 14/415* | (2006.01) |

(52) U.S. Cl.
CPC ..... *C12N 15/8231* (2013.01); *C12N 15/8289* (2013.01); *A01H 6/4678* (2018.05); *A01H 6/4684* (2018.05); *C07K 14/415* (2013.01); *C12N 15/8222* (2013.01); *C12N 15/8287* (2013.01)

(58) Field of Classification Search
None
See application file for complete search history.

(56) References Cited

U.S. PATENT DOCUMENTS

| | | | |
|---|---|---|---|
| 5,478,369 | A | 12/1995 | Albertsen |
| 6,037,523 | A | 3/2000 | Albertsen |
| 6,384,304 | B1 | 5/2002 | Quandt et al. |
| 7,154,024 | B2 | 12/2006 | Albertsen |
| 2007/0044171 | A1 | 2/2007 | Kovalic et al. |
| 2007/0169227 | A1 | 7/2007 | Cigan |
| 2016/0017365 | A1 | 1/2016 | Cigan |
| 2019/0010513 | A1 | 1/2019 | Cigan |

FOREIGN PATENT DOCUMENTS

| | | |
|---|---|---|
| EP | 1405923 | 4/2004 |
| EP | 2019148 A1 | 1/2009 |
| WO | 2001060997 A2 | 8/2001 |
| WO | 2005059121 A2 | 6/2005 |
| WO | 2013138309 A1 | 9/2013 |
| WO | 2013138363 A2 | 9/2013 |
| WO | 2014039815 A2 | 3/2014 |
| WO | 2016/193798 A1 | 12/2016 |

OTHER PUBLICATIONS

Cigan, "Transcriptional gene silencing as a tool for uncovering gene function in maize", The Plant Journal, 2005, vol. 43: 929-940.
Cigan, et al. "Phenotypic complementation of ms45 maize requires tapetal expression of MS45." Sexual Plant Reproduction 14(3): 135-142 (2001).
EBI UNIPROT Accession Q4KYG9, 2005.
Kempe, "Intein-mediated protein assembly in transgenic wheat: production of active barnase and acetolactate synthase from split genes", Plant BioTech Journal, Blackwell Pub 2009, vol. 7 3:283-297.
Klahre, et al. "High molecular weight RNAs and small interfering RNAs induce systemic posttranscriptional gene silencing in plants." Proceedings of the National Academy of Sciences USA 99(18): 11981-11986 (2002).
Mette, et al. "Transcriptional silencing and promoter methylation triggered by double-stranded RNA." The EMBO Journal. (2000) 19(19):5194-5201.
Schmulling, et al. "Restoration of fertility by antisense RNA in genetically engineered male sterile tobacco plants." Molecular & General Genetics. (1993) 237(3): 385-394.
Thomas, et al. "Size constraints for targeting post-transcriptional gene silencing and for RNA-directed methylation in Nicotiana benthamiana using a potato virus X vector." The Plant Journal 25(4): 417-425 (2001).
International Search Report for Application No. PCT/2014/023932 dated Aug. 5, 2014.
Written Opinion for International Application No. PCT/2014/023932 dated Oct. 22, 2014.
GenBank BQ483577: "The structure and function of the expressed portion of the wheat genomes, Unstressed root cDNA library," 2002.
GenBank: CJ801823: "Comprehensive analysis of wheat ESTs in response to aluminum treatments", 2007.

(Continued)

*Primary Examiner* — David T Fox

(57) ABSTRACT

Compositions and methods for modulating male fertility in a plant are provided. Compositions comprise nucleotide sequences, and active fragments and variants thereof, which modulate male fertility. Further provided are expression cassettes comprising the male fertility polynucleotides, or active fragments or variants thereof, operably linked to a promoter, wherein expression of the polynucleotides modulates the male fertility of a plant. Various methods are provided wherein the level and/or activity of the sequences that influence male fertility is modulated in a plant or plant part. In certain embodiments, the plant is polyploid.

22 Claims, 8 Drawing Sheets

Specification includes a Sequence Listing.

(56) References Cited

OTHER PUBLICATIONS

Hill, Theresa A.; et al.: "Discrete spatial and temporal cis-acting elements regulate transcription of the *Arabidopsis* floral homeotic gene APETALA3", Development, 1998, vol. 125, pp. 1711-1721.
Li, Zhijian T.; et al.: "Bi-directional duplex promoters with duplicated enhancers significantly increase transgene expression in grape and tobacco", Transgenic Research, 2004, vol. 13, pp. 143-154.

```
WHEAT CONSENSUS 500bp    (1)   TCTAATCTTCTTACAATTATCTCCATAACAACTGCTAATAACTAAATCATTATCACGAATGAGGCTGAATTCTTGACTTCTCCCTTGCTCTTCTGCTTCT
ZmMS45 promoter 500 bp   (1)   -----TAGAGTTGCCAGACTAGCCCTAGAAGTGTTTTCCCAA-TAAATTACAATCAC---TGTGTATAATTATTGGCCAGCCCCATAAA------TTAT
               Consensus (1)        T      TT C A  T CC TA  A T T  AA TAAAT A ATCAC  TG G  T A T  TTG C    CCC T            TT T                                                                                                                                                                                 100

101                                                                                                200
WHEAT CONSENSUS 500bp    (101) TTCTCCTCCAAAGTTGCTCTTCTCTCCCTGTATACTGATCC--T-CACCAGATCAGTCATGCATGAAAATTGGCTCGGTATNNCCTCCTGGATCACTT
ZmMS45 promoter 500 bp   (85)  TTAAAC-CGAAACTGAAATCGAGCGAAACCAAAT-CTGAGCTATTTCTCTAGATTAGTAAAA--AGGGAGAGAGGAAGAGAAATCAGTTTAAGTCAT
               Consensus (101) TT   CC AAA T    TC            C      AT CTGA C     T C C AGAT AG    A  AGAA G        G     C    T A   CT 201                                                                                                300
WHEAT CONSENSUS 500bp    (198) TATGCTTGACCTGTACA-TCTTTGCATCACTATCCAA-GCAACGAAGGCATGCAAGTCCCAAATTCCAAAAGGCGCCATATCCCCTTAGCTGTCTGAACCG
ZmMS45 promoter 500 bp   (181) TGTCCCTGAGATGTGCGGTTTGGCAACGATAGCACCGTAATCATAGCTCATAGGTGCCTACGTC-AGTTCGGCAGCTCTCGTG---TCATCTCACATG
               Consensus (201) T T C TGA  TGT C  T T GCA C  TA CCA   G AA  A  GC      A GT CC A   TC A       CG CA  TC C T   T  TCT A  G 301                                                                                                400
WHEAT CONSENSUS 500bp    (296) AAATAC-ACCTACTCC--CAAAACGATCACACCGACCCAT-GCAACCTCCGTGCGTGT-------CGGGATAAT--CTTGTGACG------CTAGCTGACT
ZmMS45 promoter 500 bp   (277) GCATACTACATGCTTGTTCAACCGTTCGTCTTGTTCCATCGCCTCCAAGCCTTGCCTATTCTGAACCAAGAGAGATACCTACTCCCAAACAATCCATCTTACT
               Consensus (301) ATAC AC T  CT     CAA  CG TC         CAA  G    CCAT G       CC TGC T T   C  GA  AT  CT  C      C A CT ACT 401                                                                                                500
WHEAT CONSENSUS 500bp    (377) CATGCAACTCCCGTGCGTGT-CGGA-ATATATTTTCGGAGCAAATCCATTAA-GAATTTAAGATC-ACATTGCCCGCGCTTTTTNCGTCTGCATGCAAA
ZmMS45 promoter 500 bp   (377) CATGCAACTTCCATGCAACACCACACATATGTTTCCTGAACCAATCCATTAAAGATCACAACAGCTAGCGTTCCCGCTAGCTTCCCTCT--TCCTCT
               Consensus (401) CATGCAACT  CC TGC       CG A ATAT TTT C GA C AATCCATTAA    AA  A  C A     TC C C CGCT   TT C TCT T C 501       528
WHEAT CONSENSUS 500bp    (473) ACAGAGCCACTGCCCTCTACCTCCATGG
ZmMS45 promoter 500 bp   (475) GCCGATCTTTTTCG-TCCACCACCATG-
               Consensus (501) C GA C  T C  TC ACC  CCATG
```

FIG. 2

```
                            1                                                                                               100
Wheat pIR sequence   (1)   CTCTAATCTTCTTACAATTATCTCCATAACAACTGCTAATAACTAAATCATTATCACGAATGAGGCT-AATTCTTGACTTCTCCCTTGCTTCTCTGCTTC
WHEAT CONSENSUS 500bp (1)  -TCTAATCTTCTTACAATTATCTCCATAACAACTGCTAATAACTAAATCATTATCACGAATGAGGCTGAATTCTTGACTTCTCCCTTGCTTCTCTGCTTC
          Consensus  (1)    TCTAATCTTCTTACAATTATCTCCATAACAACTGCTAATAACTAAATCATTATCACGAATGAGGCT AATTCTTGACTTCTCCCTTGCTTCTCTGCTTC 101                                                                                             200
Wheat pIR sequence   (100) TTTCTCCTCCAAAGTTTGCTCTTCTCCCTGTATACTGATCCTCACCAGATCAGTCATGCATGAAAATTGGCTCGGTAT--CCTCCTGGATCACTTTA
WHEAT CONSENSUS 500bp (100) TTTCTCCTCCAAAGTTTGCTCTTCTCCCTGTATACTGATCCTCACCAGATCAGTCATGCATGAAAATTGGCTCGGTATNNCCTCCTGGATCACTTTA
          Consensus  (101) TTTCTCCTCCAAAGTTTGCTCTTCTCCCTGTATACTGATCCTCACCAGATCAGTCATGCATGAAAATTGGCTCGGTAT  CCTCCTGGATCACTTTA 201                                                                                             300
Wheat pIR sequence   (198) TGCTTGTTGACCTGTACATCTTGCATCATCACTATCCAAGCAACGAAGGCATGCAAGTCCCAAATTCCAAAAGCGCCATATCCCCTTAGCTGTTCTGAACCGA
WHEAT CONSENSUS 500bp (200) TGCTTG---ACCTGTACATCTTGCATCATCACTATCCAAGCAACGAAGGCATGCAAGTCCCAAATTCCAAAAGCGCCATATCCCCTTAGCTGTTCTGAACCGA
          Consensus  (201) TGCTTG   ACCTGTACATCTTGCATCATCACTATCCAAGCAACGAAGGCATGCAAGTCCCAAATTCCAAAAGCGCCATATCCCCTTAGCTGTTCTGAACCGA 301                                                                                             400
Wheat pIR sequence   (298) AATACACCTACTCCCAAACGATCACACCGACCCATGCAACCTCCGTGCGTGCGGGATAATCTTGTGACGCTAGCTGACTCATGCAACTCCCGTGCATGT
WHEAT CONSENSUS 500bp (297) AATACACCTACTCCCAAACGATCACACCGACCCATGCAACCTCCGTGCCTGCGTGCGGGATAATCTTGTGACGCTAGCTGACTCATGCAACTCCCGTGCGTGT
          Consensus  (301) AATACACCTACTCCCAAACGATCACACCGACCCATGCAACCTCCGTGCCTGCGTGCGGGATAATCTTGTGACGCTAGCTGACTCATGCAACTCCCGTGC TGT 401                                                                                             500
Wheat pIR sequenc    (398) CGGAATATATTTTCGGAGCAAATCCATTAAGAATTAAGATCACA------------------------------------------------
WHEAT CONSENSUS 500bp (397) CGGAATATATTTTCGGAGCAAATCCATTAAGAATTAAGATCACATTGCCCGCGCTTTTTTNCGTCTGCATGCAAAAACAGAGCCACTGCCCCTCTACCTCC
          Consensus  (401) CGGAATATATTTTCGGAGCAAATCCATTAAGAATTAAGATCACA 501
Wheat pIR sequence   (443) ----
WHEAT CONSENSUS 500bp (497) ATGG
          Consensus  (501)
```

FIG. 3

SEQUENCE LISTING

<160> NUMBER OF SEQ ID NOS: 17

<210> SEQ ID NO 1
<211> LENGTH: 916
<212> TYPE: DNA
<213> ORGANISM: Triticum aestivum

<400> SEQUENCE: 1

| | | | | | |
|---|---|---|---|---|---|
| ctataaaaat | aagcaccggt | gcttgagaaa | aatccggttt | attttttgtaa | gcacctctcc | 60 |
| taagcacctt | gcattgtaca | aggtcttgga | gaaataaacc | aggctttctt | taagtatccg | 120 |
| tgcttattta | tacaggacag | acgcttaatt | agacgtttct | cctgtagaaa | taggcacaaa | 180 |
| tgcttcaaaa | aaatccgatt | tgtttttata | agcacctagc | attgtacgag | gccttacgta | 240 |
| tttgttgggt | gcttaaaaag | gaagagaaag | aaagaaagaa | agcgatctag | aaatttaaac | 300 |
| actgaaggga | cccatgtcgt | caccctaggg | ccttccgaaa | cgtaggaccg | accctacacg | 360 |
| caccgcatta | cgccaattat | ctctccctct | aatccccttta | taattacctc | tataacatct | 420 |
| gtcaataact | aaatcattat | cacgaatgat | accgaattct | tgactgctcc | cttgctcttc | 480 |
| tgcttctttc | tcctccaaag | tttgctcttc | tctccctgat | cctgatcctc | accagatcag | 540 |
| gtcatgcatg | ataattggct | cggtatatcc | tcctggatca | ctttatgctt | gctttttttg | 600 |
| agaatccact | ttatgcttgt | tgacctgtac | atcttgcatc | actatccaag | caacgaaggc | 660 |
| atgcaaatcc | caaattccaa | aagcgccata | tcccctttagc | tgttctgaac | cgaaatacac | 720 |
| ctactcccaa | acgatcacac | cgacccatgc | aacctccgtg | cgtgccggga | taatattgtc | 780 |
| acgctagctg | actcatgcaa | ctcccgtgca | tgtcggtata | tattttcggg | gcaaatccat | 840 |
| taagaattta | agatcacatt | gcccgcgctt | ttttcgtccg | catgcaaact | agagccactg | 900 |
| ccctctacct | ccatgg | | | | | 916 |

<210> SEQ ID NO 2
<211> LENGTH: 939
<212> TYPE: DNA
<213> ORGANISM: Triticum aestivum

<400> SEQUENCE: 2

| | | | | | |
|---|---|---|---|---|---|
| aagcatcggt | gcttatttat | acatggcaga | cgcttaatag | acgctctcct | gtaaaaataa | 60 |
| gcacccgtgc | tttagaaaaa | tccggtttat | ttttgtaagc | acctctccta | agcaccttgc | 120 |
| attgtacaag | gccttggaga | aataaagcag | gctttctta | agtatcggtg | cttatttgta | 180 |
| caggtcagac | gcttaattag | gcgtctctcc | tgtagaaata | ggcaccgatg | acttcaaaaa | 240 |
| aaaacccgct | ctatttttc | taagcacata | acattgtaca | agaccttaag | catttgtcgg | 300 |
| gtgcttaaaa | gaaagaaaaa | gaaagaaaga | atgcgatctg | aaaatttaaa | cactgaaggg | 360 |
| acccatgtcg | tcgccctagg | gccttcctaa | acgtaggacc | gaccctgcat | gcaccgcatt | 420 |
| acgccaatta | tctctccctc | taatcttctt | acaattatct | ccataacaac | tgctaataac | 480 |
| taaatcatta | tcacgaatga | ggctgaattc | ttgacttctc | ccttgctctt | ctgcttcttt | 540 |
| ctcctccaaa | gtttgctctt | ctctccctgt | atactgatcc | tcaccagatc | aggtcatgca | 600 |
| tgaaaattgg | ctcggtatcc | tcctggatca | ctttatgctt | gttgacctgt | acatcttgca | 660 |
| tcactatcca | agcaacgaag | gcatgcaagt | cccaaattcc | aaaagcgcca | tatccccttta | 720 |
| gctgttctga | accgaaatac | acctactccc | aaacgatcac | accgacccat | gcaacctccg | 780 |
| tgcgtgtcgg | gataatcttg | tgacgctagc | tgactcatgc | aactcccgtg | cgtgtcggaa | 840 |
| tatattttcg | gagcaaatcc | attaagaatt | taagatcaca | ttgcccgcgc | tttttttcgt | 900 |

```
ctgcatgcaa acagagcca ctgccctcta cctccatgg         939
```

<210> SEQ ID NO 3
<211> LENGTH: 994
<212> TYPE: DNA
<213> ORGANISM: Triticum aestivum
<220> FEATURE:
<221> NAME/KEY: misc_feature
<222> LOCATION: (784)..(784)
<223> OTHER INFORMATION: n is a, c, g, or t

<400> SEQUENCE: 3

```
aaccatactt tcttaagca tcggtgctta tttatacatg gcagacgctt aattagacgc    60
ctctcctgta aaataagca cccgtgcttt agaaaaatcc ggtttatttt tgtaagcacc   120
tctcctaagc accttgcatt gtacaaggcc ttggagaaat aaagcaggct ttctttaagt   180
atcggtgctt atttgtacag gtcagacgct taattaggcg tctctcctgt agaaataggc   240
accgatgctt caaaaaaaaa cccgctctat ttttctaagc ataacatt gtacaagacc    300
ttaagcattt gtcgggtgct aaaagaaag aaaagaaag aaagaatgcg atctgaaaat    360
ttaaacactg aagggaccca tgtcgtcgcc ctagggcctt cctaaacgta ggaccgaccc    420
tgcatgcacc gcattacgcc aattatctct ccctctaatc ttcttacaat tatctccata    480
acaactgcta ataactaaat cattatcacg aatgaggctg aattcttgac ttctcccttg    540
ctcttctgct tctttctcct ccaaagtttg ctcttctctc cctgtatact gatcctcacc    600
agatcaggtc atgcatgaaa attggctcgg tatcctcctg gatcacttta tgcttgttga    660
cctgtacatc ttgcatcact atccaagcaa cgaaggcatg caagtcccaa attccaaaag    720
cgccatatcc ccttagctgt tctgaaccga aatacaccta ctcccaaacg atcacacctc    780
gccngaaccg aaatacacct actcccaaac gatcacaccg acccatgcaa cctccgtgcg    840
tgtcgggata tcttgtgac gctagctgac tcatgcaact cccgtgcgtg tcggaatata    900
ttttcggagc aaatccatta agaatttaag atcacattgc ccgcgctttt ttcgtctgca    960
tgcaaaacag agccactgcc ctctacctcc atgg                                994
```

<210> SEQ ID NO 4
<211> LENGTH: 500
<212> TYPE: DNA
<213> ORGANISM: Triticum aestivum
<220> FEATURE:
<221> NAME/KEY: misc_feature
<222> LOCATION: (181)..(182)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t

<400> SEQUENCE: 4

```
tctaatcttc ttacaattat ctccataaca actgctaata actaaatcat tatcacgaat    60
gaggctgaat tcttgacttc tcccttgctc ttctgcttct ttctcctcca agtttgctc    120
ttctctccct gtatactgat cctcaccaga tcaggtcatg catgaaaatt ggctcggtat   180
nncctcctgg atcacttat gcttgacctg tacatcttgc atcactatcc aagcaacgaa   240
ggcatgcaag tcccaaattc caaagcgcc atatcccctt agctgttctg aaccgaaata   300
cacctactcc caaacgatca caccgaccca tgcaacctcc gtgcgtgtcg ggataatctt   360
gtgacgctag ctgactcatg caactcccgt gcgtgtcgga atatattttc ggagcaaatc   420
```

```
cattaagaat ttaagatcac attgcccgcg cttttttncg tctgcatgca aaacagagcc    480
actgccctct acctccatgg                                                500

<210> SEQ ID NO 5
<211> LENGTH: 500
<212> TYPE: DNA
<213> ORGANISM: Zea mays

<400> SEQUENCE: 5
tagagttgcc agactagccc tagaatgttt tcccaataaa ttacaatcac tgtgtataat     60
tatttggcca gccccataaa ttatttaaac cgaaactgaa atcgagcgaa accaaatctg    120
agctatttct ctagattagt aaaaagggag agagagagga agaaatcagt tttaagtcat    180
tgtccctgag atgtgcggtt tggcaacgat agccaccgta atcatagctc ataggtgcct    240
acgtcaggtt cggcagctct cgtgtcatct cacatggcat actacatgct tgttcaaccg    300
ttcgtcttgt tccatcgtcc aagccttgcc tattctgaac caagaggata cctactccca    360
aacaatccat cttactcatg caacttccat gcaaacacgc acatatgttt cctgaaccaa    420
tccattaaag atcacaacag ctagcgttct cccgctagct tccctctctc ctctgccgat    480 cttttttcgtc caccaccatg                                               500

<210> SEQ ID NO 6
<211> LENGTH: 442
<212> TYPE: DNA
<213> ORGANISM: Triticum aestivum

<400> SEQUENCE: 6
ctctaatctt cttacaatta tctccataac aactgctaat aactaaatca ttatcacgaa     60
tgaggctaat tcttgacttc tcccttgctc ttctgcttct ttctcctcca agtttgctc     120 ttctctccct gtatactgat cctcaccaga tcaggtcatg catgaaaatt ggctcggtat    180
cctcctggat cactttatgc ttgttgacct gtacatcttg catcactatc caagcaacga    240
aggcatgcaa gtcccaaatt ccaaaagcgc catatcccct tagctgttct gaaccgaaat    300
acacctactc ccaaacgatc acaccgaccc atgcaacctc cgtgcgtgtc gggataatct    360
tgtgacgcta gctgactcat gcaactcccg tgcatgtcgg aatatatttt cggagcaaat    420
ccattaagaa tttaagatca ca                                             442

<210> SEQ ID NO 7
<211> LENGTH: 5804
<212> TYPE: DNA
<213> ORGANISM: Artificial
<220> FEATURE:
<223> OTHER INFORMATION: PHP54693_T-DNA

<400> SEQUENCE: 7
aagcttctct aatcttctta caattatctc cataacaact gctaataact aaatcattat     60
cacgaatgag gctaattctt gacttctccc ttgctcttct gcttctttct cctccaaagt    120
ttgctcttct ctccctgtat actgatcctc accagatcag gtcatgcatg aaaattggct    180
cggtatcctc ctggatcact ttatgcttgt tgacctgtac atcttgcatc actatccaag    240
caacgaaggc atgcaagtcc caaattccaa aagcgccata tccccttagc tgttctgaac    300
cgaaatacac ctactcccaa cgatcacacc gacccatgca acctccgtgc gtgtcggga    360 taatcttgtg acgctagctg actcatgcaa ctcccgtgca tgtcggaata tattttcgga    420
gcaaatccat taagaattta agatcacaga attcctgcag cccaaactga aggcgggaaa    480
```

```
cgacaatctg atcatgagcg gagaattaag ggagtcacgt tatgacccccc gccgatgacg    540
cgggacaagc cgttttacgt ttggaactga cagaaccgca acgattgaag gagccactca    600
gccgcgggtt tctggagttt aatgagctaa gcacatacgt cagaaaccat tattgcgcgt    660
tcaaaagtcg cctaaggtca ctatcagcta gcaaatattt cttgtcaaaa atgctccact    720
gacgttccat aaattcccct cggtatccaa ttagagtctc atattcacca tggtgtgatc    780
ttaaattctt aatggatttg ctccgaaaat atattccgac atgcacggga gttgcatgag    840
tcagctagcg tcacaagatt atcccgacac gcacggaggt tgcatgggtc ggtgtgatcg    900
tttgggagta ggtgtatttc ggttcagaac agctaagggg atatggcgct tttggaattt    960
gggacttgca tgccttcgtt gcttggatag tgatgcaaga tgtacaggtc aacaagcata   1020
aagtgatcca ggaggatacc gagccaattt tcatgcatga cctgatctgg tgaggatcag   1080
tatacaggga gagaagagca aactttggag gagaaagaag cagaagagca agggagaagt   1140
caagaattag cctcattcgt gataatgatt tagttattag cagttgttat ggagataatt   1200
gtaagaagat tagaggcggc cgcgggtcta gaccatggtg gatcctctag agtcgacctg   1260
cagaagtaac accaaacaac agggtgagca tcgacaaaag aaacagtacc aagcaaataa   1320
atagcgtatg aaggcagggc taaaaaaatc cacatatagc tgctgcatat gccatcatcc   1380
aagtatatca agatcaaaat aattataaaa catacttgtt tattataata gataggtact   1440
caaggttaga gcatatgaat agatgctgca tatgccatca tgtatatgca tcagtaaaac   1500
ccacatcaac atgtataccT atcctagatc gatatttcca tccatcttaa actcgtaact   1560
atgaagatgt atgacacaca catacagttc caaaattaat aaatacacca ggtagtttga   1620
aacagtattc tactccgatc tagaacgaat gaacgaccgc ccaaccacac cacatcatca   1680
caaccaagcg aacaaaaagc atctctgtat atgcatcagt aaaacccgca tcaacatgta   1740
tacctatcct agatcgatat ttccatccat catcttcaat tcgtaactat gaatatgtat   1800
ggcacacaca tacagatcca aaattaataa atccaccagg tagtttgaaa cagaattcta   1860
ctccgatcta gaacgaccgc ccaaccagac cacatcatca caaccaagac aaaaaaaagc   1920
atgaaaagat gacccgacaa acaagtgcac ggcatatatt gaaataaagg aaaagggcaa   1980
accaaaccct atgcaacgaa acaaaaaaaa tcatgaaatc gatcccgtct gcggaacggc   2040
tagagccatc ccaggattcc ccaaagagaa acactggcaa gttagcaatc agaacgtgtc   2100
tgacgtacag gtcgcatccg tgtacgaacg ctagcagcac ggatctaaca caaacacgga   2160
tctaacacaa acatgaacag aagtagaact accgggccct aaccatggac cggaacgccg   2220
atctagagaa ggtagagagg gggggggggg gaggacgagc ggcgtacctt gaagcggagg   2280
tgccgacggg tggatttggg ggagatctgg ttgtgtgtgt gtgcgctccg aacaacacga   2340
ggttggggaa agagggtgtg gagggggtgt ctatttatta cggcgggcga ggaagggaaa   2400
gcgaaggagc ggtgggaaag gaatcccccg tagctgccgt gccgtgagag gaggaggagg   2460
ccgcctgccg tgccggctca cgtctgccgc tccgccacgc aatttctgga tgccgacagc   2520
ggagcaagtc caacggtgga gcggaactct cgagaggggt ccagaggcag cgacagagat   2580
gccgtgccgt ctgcttcgct tggcccgacg cgacgctgct ggttcgctgg ttggtgtccg   2640
ttagactcgt cgatcgacgg cgtttaacag gctggcatta tctactcgaa acaagaaaaa   2700
tgtttcctta gtttttttaa tttcttaaag ggtatttgtt taattttttag tcactttatt   2760
ttattctatt ttatatctaa attattaaat aaaaaaacta aaatagagtt ttagttttct   2820
```

```
taatttagag gctaaaatag aataaaatag atgtactaaa aaaattagtc tataaaaacc     2880 attaaccta  aaccctaaat ggatgtacta ataaaatgga tgaagtatta taggtgaa       2940 gctatttgca aaaaaaaagg agaacacatg cacactaaaa agataaaact gtagagtcct    3000
gttgtcaaaa tactcaattg tcctttagac catgtctaac tgttcattta tatgattctc    3060
taaaacactg atattattgt agtactatag attatattat tcgtagagta agtttaaat     3120 atatgtataa agatagataa actgcacttc aaacaagtgt gacaaaaaaa atatgtggta    3180
attttttata acttagacat gcaatgctca ttatctctag agaggggcac gaccgggtca    3240
cgctgcactg caggcatgca agcttgatat cgaattccca tggagtcaaa gattcaaata    3300
gaggacctaa cagaactcgc cgtaaagact ggcgaacagt tcatacagag tctcttacga    3360
ctcaatgaca agaagaaaat cttcgtcaac atggtggagc acgacacgct tgtctactcc    3420
aaaaatatca agatacagt  ctcagaagac caaagggcaa ttgagacttt tcaacaaagg    3480
gtaatatccg aaacctcct  cggattccat tgcccagcta tctgtcactt tattgtgaag    3540
atagtggaaa aggaaggtgg ctcctacaaa tgccatcatt gcgataaagg aaaggccatc    3600
gttgaagatg cctctgccga cagtggtccc aaagatggac ccccacccac gaggagcatc    3660
gtggaaaaag aagacgttcc aaccacgtct tcaaagcaag tggattgatg tgatatctcc    3720
actgacgtaa gggatgacgc acaatcccac taagctgacc gaagctggcc gctctagaac    3780
tagatcgaat tcctgcagcc cggggatcc  agcttcgctt agttttagt  ttttggcaga    3840 aaaatgatc  aatgtttcac aaaccaaata ttttttataac ttttgatgaa agaagatcac   3900
cacggtcata tctaggggtg gtaacaaatt gcgatctaaa tgtttcttca taaaaaataa    3960
ggcttcttaa taaattttag ttcaaaataa atacgaataa agtctgattc taatctgatt    4020
cgatccttaa atttttataat gcaaaattta gagctcatta ccacctctag tcatatgtct    4080
agtctgaggt atatccaaaa agccctttct ctaaattcca cacccaactc agatgtttgc    4140
aaataaatac tccgactcca aaatgtaggt gaagtgcaac tttctccatt ttatatcaac    4200
atttgttatt ttttgtttaa catttcacac tcaaaactaa ttaataaaat acgtggttgt    4260
tgaacgtgcg cacatgtctc ccttacatta tgttttttta tttatgtatt attgttgttt    4320
tcctccgaac aacttgtcaa catatcatca ttggtcttta atatttatga atatggaagc    4380
ctagttattt acacttggct acacactagt tgtagttttg ccacttgtct aacatgcaac    4440
tctagtagtt ttgccacttg cctggcatgc aactctagta ttgacacttg tatagcatat    4500
aatgccaata cgacacctgc cttacatgaa acattatttt tgacacttgt ataccatgca    4560
acattaccat tgacatttgt ccatacacat tatatcaaat atattgagcg catgtcacaa    4620
actcgataca aagctggatg accctccctc accacatcta taaaacccg  agcgctactg    4680 taaatcactc acaacacaac acatatcttt tagtaaccttt tcaataggcg tcccccaaga    4740
actagtaacc atggccctgt ccaacaagtt catcggcgac gacatgaaga tgacctacca    4800
catggacggc tgcgtgaacg gccactactt caccgtgaag ggcgagggca gcggcaagcc    4860
ctacgagggc acccagacct ccaccttcaa ggtgaccatg ccaacggcg  gccccctggc    4920 cttctccttc gacatcctgt ccaccgtgtt catgtacggc aaccgctgct tcaccgccta    4980
ccccaccagc atgcccgact acttcaagca ggccttcccc gacggcatgt cctacgagag    5040
aaccttcacc tacgaggacg gcggcgtggc caccgccagc tgggagatca gcctgaaggg    5100
caactgcttc gagcacaagt ccaccttcca cggcgtgaac ttccccgccg acggccccgt    5160
gatggccaag aagaccaccg gctgggaccc ctccttcgag aagatgaccg tgtgcgacgg    5220
```

| | | |
|---|---|---|
| catcttgaag ggcgacgtga ccgccttcct gatgctgcag ggcggcggca actacagatg | 5280 |
| ccagttccac acctcctaca agaccaagaa gcccgtgacc atgcccccca accacgtggt | 5340 |
| ggagcaccgc atcgccagaa ccgacctgga caagggcggc aacagcgtgc agctgaccga | 5400 |
| gcacgccgtg gcccacatca cctccgtggt gcccttctga gcggcccat ggatattcga | 5460 |
| acgcgtaggt accacatggt taacctagac ttgtccatct tctggattgg ccaacttaat | 5520 |
| taatgtatga aataaaagga tgcacacata gtgacatgct aatcactata atgtgggcat | 5580 |
| caaagttgtg tgttatgtgt aattactagt tatctgaata aagagaaag agatcatcca | 5640 |
| tatttcttat cctaaatgaa tgtcacgtgt ctttataatt ctttgatgaa ccagatgcat | 5700 |
| ttcattaacc aaatccatat acatataaat attaatcata tataattaat atcaattggg | 5760 |
| ttagcaaaac aaatctagtc taggtgtgtt ttgcgaatgc ggcc | 5804 |

<210> SEQ ID NO 8
<211> LENGTH: 2079
<212> TYPE: DNA
<213> ORGANISM: Oryza sativa

<400> SEQUENCE: 8

| | | |
|---|---|---|
| atggaagaga agaagcagca gcagcagcgt ccacagagag ggcgcgatgg catcctgcag | 60 |
| tatccgcacc ttttcttcgc ggcgctggcg ctggccctgc tcctcaccga cccgttccac | 120 |
| ctcggcccgc tcgccggggt ggactaccgg ccggtgaggc acgagctggc gccgtaccgc | 180 |
| gaggtgatgg cgcggtggcc gcgggacaac ggcagccggc tcaggcacgg caggctggag | 240 |
| ttcgtcggag aggtgttcgg gccggagtcc atcgagttcg accgccacgg ccgcggcccc | 300 |
| tacgccggcc tcgccgacgg ccgcgtcgtg cggtggatgg gggaggacgc cgggtgggag | 360 |
| acgttcgccg tcatgagccc tgactggtaa cgaacacctc gcctgcattt tgctctcgcc | 420 |
| ctccacgaaa cacctctcg tagcagtgta caattacgtg ttcttatatt gcaaaaaaag | 480 |
| gtcggagaaa gtttgtgcca atggggtgga gtcgacgacg aagaagcagc acgagatgga | 540 |
| gcgacggtgc ggccggcctc tcgggctgag gtttcacggc gagaccggcg agctctacgt | 600 |
| cgccgacgcg tactacgggc tcatgtccgt cggtccgaac ggcggggtgg cgacctctct | 660 |
| cgcgagagaa gtcggcggga gcccggtcaa cttcgcgaac gacctcgaca tccaccgcaa | 720 |
| cggctccgtg ttcttcaccg acacgagcac gagatacaac agaaagtgtg cagctgcagt | 780 |
| atcactctct tcagttgtat cgattctcta tttccttcta tcgttcaaga ttttctgatt | 840 |
| agaatcagtt gtgcagggat catctgaacg ttctgctaga aggtgaaggc acagggaggc | 900 |
| tgctcagata tgacccagaa accaaagctg cccatgtcgt gctgagcggg ctggtcttcc | 960 |
| cgaatggcgt gcagatttct gacgaccagc agttcctcct cttctccgaa caacaaact | 1020 |
| gcaggtgaaa tggcacaagc tttcacaggt tctgaaaata ctaaaggtta aacaagattc | 1080 |
| agaattgatt aacattgcac gcatatgctg ttctaggata atgcggtact ggctggaagg | 1140 |
| gccaagagcc gggcaggtgg aggtgttcgc cgacctgccg gggttcccgg acaacgtgcg | 1200 |
| actgagcagc ggcggcggcg gcggccgctt ctgggtggcg atcgactgct gcaggacggc | 1260 |
| ggcgcaggag gtgttcgcca gcggccgtg gctgcgaacg ctctacttca agctgccct | 1320 |
| gacgatgcgg acgctgggga agatggtcag catgcggatg cacaccctcg tcgcgctcct | 1380 |
| cgacggcgaa ggggacgtcg tcgaggtgct cgaggaccgg ggcggcgagg tgatgcggct | 1440 |
| ggtgagcgag gtgagggagg tggggcgcaa gctgtggatc ggcaccgtgg ctcataacca | 1500 |

| | |
|---|---:|
| catcgccacg atcccttacc cgttggaaga gcagagtagc agcagcagca gcaacgtgct | 1560 |
| tggtgattga tactttgata ggctggtttt agcagcaaca aaggtgtact agttgatgta | 1620 |
| ttgtttgtgt ttgccgggcc atcatagaaa gtgcctggtg atctctggga cttgatggca | 1680 |
| aatgttgggc aaattgtgat cgaataagat tagtactaga gttatcgtgt aataaggaca | 1740 |
| tgcatggact accatgtatt tcatgttatg acgctcctaa gagccacaga ccacagtgat | 1800 |
| ggtattagac cccttctcag aatggttctg ctcattttcg gcttcgatcg tggtacgcgt | 1860 |
| tcgtgtcttc gtgtgatcgg aaaaaaaata tttgccgttt acaagtgata gttttttcagt | 1920 |
| ggatgtaatt tgtgcgaaat accatcgtac aaacgttttg ttcttttttca tcatagtcat | 1980 |
| tagcctttca tgaatagtac tcacatttat aaggccgatg gtgttgtcct ataaagaaaa | 2040 |
| aaaatgtacc agtaagtagg gtggctaacg agccaactc | 2079 |

```
<210> SEQ ID NO 9
<211> LENGTH: 488
<212> TYPE: DNA
<213> ORGANISM: Zea mays

<400> SEQUENCE: 9
```

| | |
|---|---:|
| atcgaattcc tgcagcccctt tcccaataa attacaatca ctgtgtataa ttatttggcc | 60 |
| agccccataa attatttaaa ccgaaactga atcgagcga aaccaaatct gagctatttc | 120 |
| tctagattag taaaaaggga gagagagagg aagaaatcag ttttaagtca ttgtccctga | 180 |
| gatgtgcggt ttggcaacga tagccaccgt aatcatagct cataggtgcc tacgtcaggt | 240 |
| tcggcagctc tcgtgtcatc tcacatggca tactacatgc ttgttcaacc gttcgtcttg | 300 |
| ttccatcgtc caagccttgc ctattctgaa ccaagaggat acctactccc aaacaatcca | 360 |
| tcttactcat gcaacttcca tgcaaacacg cacatatgtt tcctgaacca atccattaaa | 420 |
| gatcacaaca gctagcgttc tcccgctagc ttccctctct cctctgccga tcttttttcgt | 480 |
| ccaccacc | 488 |

```
<210> SEQ ID NO 10
<211> LENGTH: 1635
<212> TYPE: DNA
<213> ORGANISM: Oryza sativa

<400> SEQUENCE: 10
```

| | |
|---|---:|
| atgaagagcc ccatggagga agctcatgca atgccagtga catcattctt cccagtagca | 60 |
| ggaatccaca agctcatagc tatcttcctt gttgtcctct catggatctt ggtccacaag | 120 |
| tggagcctga ggaaccagaa agggccaaga tcatggccaa tcatcggcgc gacagtggag | 180 |
| caactgaaga actaccacag gatgcatgac tggcttgtcg agtacttgtc gaaggacagg | 240 |
| acggtgaccg tcgacatgcc tttcacctcc tacacctaca ttgccgaccc ggtgaacgtc | 300 |
| gagcatgtcc tgaagaccaa cttcaccaat taccccaagg gtgaagtgta caggtcttac | 360 |
| atggatgtgc tgctcggtga tggcatattc aatgccgacg cgagatgtg gaggaagcaa | 420 |
| aggaagacgg cgagcttcga gtttgcctcc aagaacttga gagacttcag cactgtggtg | 480 |
| ttcagggagt actccctgaa gctatcaagc attctgagcc aagcatgcaa ggccggcaga | 540 |
| gttgtagaca tgcaggaatt gttcatgagg atgacactgg actcgatctg caaggtcggg | 600 |
| tttgggggttg agatcgggac gctgtcacct gatctcccgg agaacagctt tgcccaggca | 660 |
| ttcgacgctc ccaacatcat cgtcacgctg cggttcatcg atcctctgtg gcgtctgaag | 720 |
| aagttcttgc acgtcggatc agaggctctc ctcgagcaga gcatgaagct ggttgatgac | 780 |

```
ttcacctaca gcgtgatccg ccgccgcaag gctgagatct tgcaggctcg agccagcggc      840
aagcaagaga agatcaagca cgacatactg tcgcggttca tcgagctcgg ggaggccggc      900
ggcgacgagg ggggcggcag cttcggggac gacaagagcc tccgcgacgt ggtgctcaac      960
ttcgtgatcg ccgggcgtga cacgacggcg acgacgctgt cgtggttcac gtacatggcg     1020
atgacgcacc cggccgtcgc cgacaagctc cggcgcgagc tggccgcgtt cgaggatgag     1080
cgcgcgcgcg aggagggcgt cgcgctcgcc gacgccgccg gcgaggcgtc gttcgcggcg     1140
cgcgtggcgc agttcgcgtc gctgctgagc tacgacgcgg tggggaagct ggtgtacctg     1200
cacgcgtgcg tgacggagac gctccgcctc tacccgcgg  tgccgcagga ccccaagggg     1260
atcgtggagg acgacgtgct ccccgacggc accaaggtgc gcgccggcgg gatggtgacg     1320
tacgtgccct actccatggg gaggatggag tacaactggg ccccgacgc  ggcgagcttc     1380 cggccggagc ggtggctcag cggcgacggc ggcgcgttcc ggaacgcgtc gccgttcaag     1440
ttcaccgcgt tccaggccgg gccgcggatc tgcctcggca aggactccgc ctacctccag     1500
atgaagatgg cgctcgccat cctcttccgc ttctacacct tcgacctcgt cgaggaccac     1560
cccgtcaagt accggatgat gaccatcctc tccatggctc acggcctcaa ggtccgcgtc     1620
tccacctccg tctga                                                      1635
```

```
<210> SEQ ID NO 11
<211> LENGTH: 837
<212> TYPE: DNA
<213> ORGANISM: Artificial
<220> FEATURE:
<223> OTHER INFORMATION: plant-optimized DAM

<400> SEQUENCE: 11
atggagaaga acagggcctt cttgaagtgg gcaggtggaa agtaccctct cctggacgac       60
atcaagcggc atctcccaaa gggcgagtgc ctggtcgaac ccttcgtggg cgctggaagc      120
gtgttcctga acaccgactt cagccgctac atcctcgcgg acatcaactc cgacctgatc      180
tccctgtaca acatcgtcaa gatgcgcacc gacgagtacg tgcaggctgc acggagcttc      240
ttcgttccgg agaccaactg cgcggaggtg tactaccagt tccgcgagga gttcaacaag      300
agccaggacc cgtttaggcg cgctgttctt ttcctctacc tgaaccgcta cggctacaac      360
ggtctttgtc gctacaatct ccgcggcgag ttcaacgtcc ccttcgggag gtacaagaag      420
ccatacttcc cggaggcaga gctctaccac ttcgcggaga aggctcagaa cgcgttcttc      480
tactgcgaga gctacgcgga ttcgatggct agggccgacg atgctagcgt tgtgtactgc      540
gacccgccgt atgcaccact gtctgccact gcaaacttca ccgcatacca caccaacagc      600
ttcaccctcg agcagcaggc gcacctcgca gaaatcgcag aaggactggt cgaacgccac      660
atcccggtcc ttatcagcaa ccacgacacc atgcttaccc gcgagtggta ccagagggcg      720
aaactccacg tggtcaaggt gcggcgcagc atatcctcca acggcggaac ccgcaagaag      780
gtcgacgagc tgctggcccct gtacaagccc ggcgtcgtga gcccagcgaa gaagtag       837
```

```
<210> SEQ ID NO 12
<211> LENGTH: 5840
<212> TYPE: DNA
<213> ORGANISM: Artificial
<220> FEATURE:
<223> OTHER INFORMATION: PHP56791 T-DNA

<400> SEQUENCE: 12
```

-continued

```
ctatgattta gaataatata caaatatatt acataaaaaa tatattaatt gaattagtgt      60
tgtctaattt ataattatta gaatgtaatt caattccaac gaaacaacgg ggccttaggt     120
ttaatatctt ccttacactg cgaaaatgtt gttacacttg ccaaaaaaaa tcaatcgcat     180 atttaccta caaggacata ttttagcaaa atgctataga catgaatcca acgtaatcaa      240
tagagtgaga tttactggta aactaccaat tgctcatctg ctcggtacca accagccttt     300
cctattacca tgcacatgtt gcctctcaac tgcagcatct ttcaagccgt gagcagacat     360
gttgcagatc gaagtaaggt atatatgtgc atagtctcct aattcttcat cttcaacctc     420
tagctgattg atctctggta tttaccactc tttccttcct tccttccttc aattctaaat     480
accacaaatc aaagttgctt tgccatggag aagaacaggg ccttcttgaa gtgggcaggt     540
ggaaagtacc ctctcctgga cgacatcaag cggcatctcc caagggcga gtgcctggtc      600 gaacccttcg tgggcgctgg aagcgtgttc ctgaacaccg acttcagccg ctacatcctc     660
gcggacatca actccgacct gatctccctg tacaacatcg tcaagatgcg caccgacgag     720
tacgtgcagg ctgcacggga gcttttcgtt ccggagacca actgcgcgga ggtgtactac     780
cagttccgcg aggagttcaa caagagccag gacccgttta ggcgcgctgt tcttttcctc     840
tacctgaacc gctacggcta caacggtctt tgtcgctaca atctccgcgg cgagttcaac     900
gtccccttcg ggaggtacaa gaagccatac ttcccggagg cagagctcta ccacttcgcg     960
gagaaggctc agaacgcgtt cttctactgc gagagctacg cggattcgat ggctagggcc    1020
gacgatgcta gcgttgtgta ctgcgacccg ccgtatgcac cactgtctgc cactgcaaac    1080
ttcaccgcat accacaccaa cagcttcacc ctcgagcagc aggcgcacct cgcagaaatc    1140
gcagaaggac tggtcgaacg ccacatcccg gtccttatca gcaaccacga caccatgctt    1200
acccgcgagt ggtaccagag ggcgaaactc cacgtggtca aggtgcggcg cagcatatcc    1260
tccaacggcg gaacccgcaa gaaggtcgac gagctgctgg ccctgtacaa gcccggcgtc    1320
gtgagcccag cgaagaagta gtagttaacc tagacttgtc catcttctgg attggccaac    1380
ttaattaatg tatgaaataa aaggatgcac acatagtgac atgctaatca ctataatgtg    1440
ggcatcaaag ttgtgtgtta tgtgtaatta ctagttatct gaataaaaga gaaagagatc    1500
atccatattt cttatcctaa atgaatgtca cgtgtcttta taattctttg atgaaccaga    1560
tgcatttcat taaccaaatc catatacata taaatattaa tcatatataa ttaatatcaa    1620
ttgggttagc aaaacaaatc tagtctaggt gtgttttgcg aattgcggcc gctctagaac    1680
tagtggatcc cccgggctgc aggaattccc atggagtcaa agattcaaat agaggaccta    1740
acagaactcg ccgtaaagac tggcgaacag ttcatacaga gtctcttacg actcaatgac    1800
aagaagaaaa tcttcgtcaa catggtggag cacgacacgc ttgtctactc caaaaatatc    1860
aaagatacag tctcagaaga ccaaagggca attgagactt ttcaacaaag ggtaatatcc    1920
ggaaacctcc tcggattcca ttgcccagct atctgtcact ttattgtgaa gatagtggaa    1980
aaggaaggtg gctcctacaa atgccatcat tgcgataaag gaaaggccat cgttgaagat    2040
gcctctgccg acagtggtcc caaagatgga cccccaccca cgaggagcat cgtggaaaaa    2100
gaagacgttc caaccacgtc ttcaaagcaa gtggattgat gtgatatctc cactgacgta    2160
agggatgacg cacaatccca ctaaagcttg catgcctgca gtgcagcgtg acccggtcgt    2220 gccctctct agagataatg agcattgcat gtctaagtta taaaaaatta ccacatattt    2280 ttttgtcac acttgtttga agtgcagttt atctatcttt atacatatat ttaaacttta    2340
ctctacgaat aatataatct atagtactac aataatatca gtgttttaga gaatcatata    2400
```

```
aatgaacagt tagacatggt ctaaaggaca attgagtatt ttgacaacag gactctacag    2460
ttttatcttt ttagtgtgca tgtgttctcc tttttttttg caaatagctt cacctatata    2520
atacttcatc cattttatta gtacatccat ttagggttta gggttaatgg ttttttataga   2580 ctaatttttt tagtacatct atttttattct attttagcct ctaaattaag aaaactaaaa   2640
ctctatttta gttttttttat ttaataattt agatataaaa tagaataaaa taaagtgact   2700
aaaaattaaa caaatacccct ttaagaaatt aaaaaaacta aggaaacatt tttcttgttt   2760
cgagtagata atgccagcct gttaaacgcc gtcgacgagt ctaacggaca ccaaccagcg    2820
aaccagcagc gtcgcgtcgg gccaagcgaa gcagacggca cggcatctct gtcgctgcct    2880
ctggacccct ctcgagagtt ccgctccacc gttggacttg ctccgctgtc ggcatccaga    2940
aattgcgtgg cggagcggca gacgtgagcc ggcacggcag gcggcctcct cctcctctca    3000
cggcaccggc agctacgggg gattcctttc ccaccgctcc ttcgcttttcc cttcctcgcc   3060 cgccgtaata aatagacacc ccctccacac cctctttccc caacctcgtg ttgttcggag    3120
cgcacacaca cacaaccaga tctcccccaa atccaccccgt cggcacctcc gcttcaaggt   3180
acgccgctcg tcctcccccc ccccctctc taccttctct agatcggcgt tccggtccat     3240
gcatggttag ggcccggtag ttctacttct gttcatgttt gtgttagatc cgtgtttgtg    3300
ttagatccgt gctgctagcg ttcgtacacg gatgcgacct gtacgtcaga cacgttctga    3360
ttgctaactt gccagtgttt ctctttgggg aatcctggga tggctctagc cgttccgcag    3420
acgggatcga tttcatgatt ttttttgttt cgttgcatag ggtttggttt gcccttttcc    3480
tttatttcaa tatatgccgt gcacttgttt gtcgggtcat cttttcatgc ttttttttgt    3540
cttggttgtg atgatgtggt ctggttgggc ggtcgttcta gatcggagta gaattctgtt    3600
tcaaactacc tggtggattt attaattttg gatctgtatg tgtgtgccat acatattcat    3660
agttacgaat tgaagatgat ggatggaaat atcgatctag gataggtata catgttgatg    3720
cgggttttac tgatgcatat acagagatgc ttttttgttcg cttggttgtg atgatgtggt   3780
gtggttgggc ggtcgttcat tcgttctaga tcggagtaga atactgtttc aaactacctg    3840
gtgtatttat taattttgga actgtatgtg tgtgtcatac atcttcatag ttacgagttt    3900
aagatggatg gaaatatcga tctaggatag gtatacatgt tgatgtgggt tttactgatg    3960
catatacatg atggcatatg cagcatctat tcatatgctc taaccttgag tacctatcta    4020
ttataataaa caagtatgtt ttataattat tttgatcttg atatacttgg atgatggcat    4080
atgcagcagc tatatgtgga tttttttagc cctgccttca tacgctattt atttgcttgg    4140
tactgtttct tttgtcgatg ctcaccctgt tgtttggtgt tacttctgca ggtcgacttt    4200
aacttagcct aggatccaca cgacaccatg tcccccgagc gccgcccgt cgagatccgc     4260 ccggccaccg ccgccgacat ggccgccgtg tgcgacatcg tgaaccacta catcgagacc    4320
tccaccgtga acttccgcac cgagccgcag acccccagg agtggatcga cgacctggag    4380
cgcctccagg accgctaccc gtggctcgtg gccgaggtgg agggcgtggt ggccggcatc    4440
gcctacgccg gcccgtggaa ggcccgcaac gcctacgact ggaccgtgga gtccaccgtg    4500
tacgtgtccc accgccacca gcgcctcggc ctcggctcca ccctctacac ccacctcctc    4560
aagagcatgg aggcccaggg cttcaagtcc gtggtggccg tgatcggcct cccgaacgac    4620
ccgtccgtgc gcctccacga ggccctcggc tacaccgccc gcggcaccct ccgcgccgcc    4680
ggctacaagc acggcggctg gcacgacgtc ggcttctggg agcgcgactt cgagctgccg    4740
```

```
gccccgccgc gcccggtgcg cccggtgacg cagatctccg gtggaggcgg cagcggtggc    4800
ggaggctccg gaggcggtgg ctccatggcc tcctccgagg acgtcatcaa ggagttcatg    4860
cgcttcaagg tgcgcatgga gggctccgtg aacggccacg agttcgagat cgagggcgag    4920
ggcgagggcc gcccctacga gggcacccag accgccaagc tgaaggtgac caagggcggc    4980
cccctgccct cgcctggga catcctgtcc ccccagttcc agtacggctc caaggtgtac    5040
gtgaagcacc ccgccgacat ccccgactac aagaagctgt ccttccccga gggcttcaag    5100
tgggagcgcg tgatgaactt cgaggacggc ggcgtggtga ccgtgaccca ggactcctcc    5160
ctgcaggacg gctccttcat ctacaaggtg aagttcatcg gcgtgaactt ccctccgac    5220
ggccccgtaa tgcagaagaa gactatgggc tgggaggcct ccaccgagcg cctgtacccc    5280
cgcgacggcg tgctgaaggg cgagatccac aaggccctga gctgaagga cggcggccac    5340
tacctggtgg agttcaagtc catctacatg gccaagaagc ccgtgcagct gcccggctac    5400
tactacgtgg actccaagct ggacatcacc tcccacaacg aggactacac catcgtggag    5460
cagtacgagc gcgccgaggg ccgccaccac ctgttcctgt agtcaggatc tgagtcgaaa    5520
cctagacttg tccatcttct ggattggcca acttaattaa tgtatgaaat aaaaggatgc    5580
acacatagtg acatgctaat cactataatg tgggcatcaa agttgtgtgt tatgtgtaat    5640
tactagttat ctgaataaaa gagaaagaga tcatccatat ttcttatcct aaatgaatgt    5700
cacgtgtctt tataattctt tgatgaacca gatgcatttc attaaccaaa tccatataca    5760
tataaatatt aatcatatat aattaatatc aattgggtta gcaaacaaa tctagtctag    5820
gtgtgttttg cgaatgcggc                                               5840

<210> SEQ ID NO 13
<211> LENGTH: 6897
<212> TYPE: DNA
<213> ORGANISM: Artificial
<220> FEATURE:
<223> OTHER INFORMATION: PHP54783 T-DNA

<400> SEQUENCE: 13
aagcttgcct gcgaaaatgt tgttacactt gccaaaaaaa atcaatcgca tatttacctt      60
acaaggacat attttagcaa aatgctatag acatgaatcc aacgtaatca atagagtgag     120
atttactggt aaaactaccaa ttgctcatct gctcggtacc aaccagcctt tcctattacc     180
atgcacatgt tgcctctcaa ctgcagcatc tttcaagccg tgagcagaca tgttgcagat     240
cgaagtaagg tatatatgtg catagtctcc taattcttca tcttcaacct ctagctgatt     300
gatctctggt atttaccact ctttccttcc ttccttcctt caattctaaa taccacaaat     360
caaagttgct ttggaattcc tgcagcccaa actgaaggcg ggaacgaca atctgatcat     420
gagcggagaa ttaagggagt cacgttatga ccccgccga tgacgcggga caagccgttt     480
tacgtttgga actgacagaa ccgcaacgat tgaaggagcc actcagccgc gggtttctgg     540
agtttaatga gctaagcaca tacgtcagaa accattattg cgcgttcaaa agtcgcctaa     600
ggtcactatc agctagcaaa tatttcttgt caaaaatgct ccactgacgt tccataaatt     660
cccctcggta tccaattaga gtctcatatt caccatgaca aagcaacttt gatttgtggt     720
atttagaatt gaaggaagga aggaaggaaa gagtggtaaa taccagagat caatcagcta     780
gaggttgaag atgaagaatt aggagactat gcacatatat accttacttc gatctgcaac     840
atgtctgctc acggcttgaa agatgctgca gttgagaggc aacatgtgca tggtaatagg     900
aaaggctggt tggtaccgag cagatgagca attggtagtt taccagtaaa tctcactcta     960
```

```
ttgattacgt tggattcatg tctatagcat tttgctaaaa tatgtccttg taaggtaaat   1020
atgcgattga tttttttttgg caagtgtaac aacattttcg caggcggccg cgggtctaga   1080
ccatggtgga tccggatcct ctagagtcga cctgcagaag taacaccaaa caacagggtg   1140
agcatcgaca aaagaaacag taccaagcaa ataaatagcg tatgaaggca gggctaaaaa   1200
aatccacata tagctgctgc atatgccatc atccaagtat atcaagatca aaataattat   1260
aaaacatact tgtttattat aatagatagg tactcaaggt tagagcatat gaatagatgc   1320
tgcatatgcc atcatgtata tgcatcagta aaacccacat caacatgtat acctatccta   1380
gatcgatatt tccatccatc ttaaactcgt aactatgaag atgtatgaca cacacataca   1440
gttccaaaat taataaatac accaggtagt ttgaaacagt attctactcc gatctagaac   1500
gaatgaacga ccgcccaacc acaccacatc atcacaacca agcgaacaaa aagcatctct   1560
gtatatgcat cagtaaaacc cgcatcaaca tgtataccta tcctagatcg atatttccat   1620
ccatcatctt caattcgtaa ctatgaatat gtatggcaca cacatacaga tccaaaatta   1680
ataaatccac caggtagttt gaaacagaat tctactccga tctagaacga ccgcccaacc   1740
agaccacatc atcacaacca agacaaaaaa aagcatgaaa agatgacccg acaaacaagt   1800
gcacggcata tattgaaata aaggaaaagg gcaaaccaaa ccctatgcaa cgaaacaaaa   1860
aaaatcatga aatcgatccc gtctgcggaa cggctagagc catcccagga ttccccaaag   1920
agaaacactg gcaagttagc aatcagaacg tgtctgacgt acaggtcgca tccgtgtacg   1980
aacgctagca gcacggatct aacacaaaca cggatctaac acaaacatga acagaagtag   2040
aactaccggg ccctaaccat ggaccggaac gccgatctag agaaggtaga gagggggggg   2100
gggggaggac gagcggcgta ccttgaagcg gaggtgccga cgggtggatt tgggggagat   2160
ctggttgtgt gtgtgtgcgc tccgaacaac acgaggttgg ggaaagaggg tgtggagggg   2220
gtgtctattt attacggcgg gcgaggaagg gaaagcgaag gagcggtggg aaaggaatcc   2280
cccgtagctg ccgtgccgtg agaggaggag gaggccgcct gccgtgccgg ctcacgtctg   2340
ccgctccgcc acgcaatttc tggatgccga cagcggagca agtccaacgg tggagcggaa   2400
ctctcgagag gggtccagag gcagcgacag agatgccgtg ccgtctgctt cgcttggccc   2460
gacgcgacgc tgctggttcg ctggttggtg tccgttagac tcgtcgatcg acggcgttta   2520
acaggctggc attatctact cgaaacaaga aaaatgtttc cttagttttt ttaatttctt   2580
aaagggtatt tgtttaattt ttagtcactt tattttattc tattttatat ctaaattatt   2640
aaataaaaaa actaaaatag agtttttagtt ttcttaattt agaggctaaa atagaataaa   2700
atagatgtac taaaaaaatt agtctataaa aaccattaac cctaaaccct aaatggatgt   2760
actaataaaa tggatgaagt attatatagg tgaagctatt tgcaaaaaaa aaggagaaca   2820
catgcacact aaaaagataa aactgtagag tcctgttgtc aaaatactca attgtccttt   2880
agaccatgtc taactgttca tttatatgat tctctaaaac actgatatta ttgtagtact   2940
atagattata ttattcgtag agtaaagttt aaatatatgt ataaagatag ataaactgca   3000
cttcaaacaa gtgtgacaaa aaaaatatgt ggtaattttt tataacttag acatgcaatg   3060
ctcattatct ctagagaggg gcacgaccgg gtcacgctgc actgcaggca tgcaagcttc   3120
cccctcgagg tcgacggtat cgataagctt gatatcgaat tcccatggag tcaaagattc   3180
aaatagagga cctaacagaa ctcgccgtaa agactggcga acagttcata cagagtctct   3240
tacgactcaa tgcaagaag aaaatcttcg tcaacatggt ggagcacgac acgcttgtct   3300
```

```
actccaaaaa tatcaaagat acagtctcag aagaccaaag ggcaattgag acttttcaac    3360
aaagggtaat atccggaaac ctcctcggat tccattgccc agctatctgt cactttattg    3420
tgaagatagt ggaaaaggaa ggtggctcct acaaatgcca tcattgcgat aaaggaaagg    3480
ccatcgttga agatgcctct gccgacagtg gtcccaaaga tggacccccca cccacgagga    3540 gcatcgtgga aaagaagac gttccaacca cgtcttcaaa gcaagtggat tgatgtgata    3600
tctccactga cgtaagggat gacgcacaat cccactaagc tgaccgaagc tggccgctct    3660
agaactagat cgaattcctg cagcccatcc ctcagccgcc tttcactatc ttttttgccc    3720
gagtcattgt catgtgaacc ttggcatgta taatcggtga attgcgtcga ttttcctctt    3780
ataggtgggc caatgaatcc gtgtgatcgc gtctgattgg ctagagatat gtttcttcct    3840
tgttggatgt attttcatac ataatcatat gcatacaaat atttcattac actttataga    3900
aatggtcagt aataaaccct atcactatgt ctggtgtttc attttatttg cttttaaacg    3960
aaaattgact tcctgattca atatttaagg atcgtcaacg gtgtgcagtt actaaattct    4020
ggtttgtagg aactatagta aactattcaa gtcttcactt attgtgcact cacctctcgc    4080
cacatcacca cagatgttat tcacgtctta aatttgaact acacatcata ttgacacaat    4140
atttttttta aataagcgat taaaacctag cctctatgtc aacaatggtg tacataacca    4200
gcgaagttta gggagtaaaa aacatcgcct tacacaaagt tcgctttaaa aaataaagag    4260
taaattttac tttggaccac ccttcaacca atgtttcact ttagaacgag taattttatt    4320
attgtcactt tggaccaccc tcaaatcttt tttccatcta catccaattt atcatgtcaa    4380
agaaatggtc tacatacagc taaggagatt tatcgacgaa tagtagctag catactcgag    4440
gtcattcata tgcttgagaa gagagtcggg atagtccaaa ataaaacaaa ggtaagatta    4500
cctggtcaaa agtgaaaaca tcagttaaaa ggtggtataa agtaaaatat cggtaataaa    4560
aggtggccca aagtgaaatt tactctttc tactattata aaaattgagg atgttttgt    4620 cggtactttg atacgtcatt tttgtatgaa ttggtttta agtttattcg cttttggaaa    4680
tgcatatctg tatttgagtc gggttttaag ttcgtttgct tttgtaaata cagagggatt    4740
tgtataagaa atatctttaa aaaaacccat atgctaattt gacataattt ttgagaaaaa    4800
tatatattca ggcgaattct cacaatgaac aataataaga ttaaaatagc tttcccccgt    4860
tgcagcgcat gggtattttt tctagtaaaa ataaaagata aacttagact caaaacattt    4920
acaaaaacaa cccctaaagt tcctaaagcc caaagtgcta tccacgatcc atagcaagcc    4980
cagcccaacc caacccaacc caacccaccc cagtccagcc aactggacaa tagtctccac    5040 accccccac tatcaccgtg agttgtccgc acgcaccgca cgtctcgcag ccaaaaaaaa    5100 aaaagaaag aaaaaaaga aaagaaaaa acagcaggtg ggtccgggtc gtgggggccg    5160
gaaacgcgag gaggatcgcg agccagcgac gaggccggcc ctccctccgc ttccaaagaa    5220
acgcccccca tcgccactat atacataccc ccccctctcc tcccatcccc caacccctac    5280
caccaccacc accaccacct ccacctcctc ccccctcgct gccggacgac gagctcctcc    5340
cccctccccc tccgccgccg ccgcgccggt aaccacccg cccctctcct ctttctttct    5400 ccgtttttt tttccgtctc ggtctcgatc tttggcttg gtagtttggg tgggcgagag    5460
gcggcttcgt gcgcgcccag atcggtgcgc gggaggggcg ggatctcgcg gctggggctc    5520
tcgccggcgt ggatcaggcc cggatctcgc ggggaatggg gctctcggat gtagatctgc    5580
gatccgccgt tgttggggga gatgatgggg ggtttaaaat ttccgccatg ctaaacaaga    5640
tcaggaagag gggaaaaggg cactatggtt tatatttta tatatttctg ctgcttcgtc    5700
```

-continued

```
aggcttagat gtgctagatc tttctttctt cttttgtgg gtagaatttg aatccctcag      5760
cattgttcat cggtagtttt tcttttcatg atttgtgaca aatgcagcct cgtgcggagc      5820 tttttgtag gtagaaggat ccaccggtcg ccaccatggc cctgtccaac aagttcatcg       5880
gcgacgacat gaagatgacc taccacatgg acggctgcgt gaacggccac tacttcaccg      5940
tgaagggcga gggcagcggc aagccctacg agggcaccca gacctccacc ttcaaggtga      6000
ccatggccaa cggcggcccc ctggccttct ccttcgacat cctgtccacc gtgttcatgt      6060
acggcaaccg ctgcttcacc gcctacccca ccagcatgcc cgactacttc aagcaggcct      6120
tccccgacgg catgtcctac gagagaacct tcacctacga ggacggcggc gtggccaccg      6180
ccagctggga gatcagcctg aagggcaact gcttcgagca aagtccacc ttccacggcg       6240 tgaacttccc cgccgacggc cccgtgatgg ccaagaagac caccggctgg gacccctcct      6300
tcgagaagat gaccgtgtgc gacggcatct gaagggcga cgtgaccgcc ttcctgatgc      6360
tgcagggcgg cggcaactac agatgccagt ccacaccctc ctacaagacc aagaagcccg      6420
tgaccatgcc ccccaaccac gtggtggagc accgcatcgc cagaaccgac ctggacaagg      6480
gcggcaacag cgtgcagctg accgagcacg ccgtggccca catcacctcc gtggtgccct      6540
tctgaagcgg cccatggata ttcgaacgcg taggtaccga cttgtccatc ttctggattg      6600
gccaacttaa ttaatgtatg aaataaaagg atgcacacat agtgacatgc taatcactat      6660
aatgtgggca tcaaagttgt gtgttatgtg taattactag ttatctgaat aaaagagaaa      6720
gagatcatcc atatttctta tcctaaatga atgtcacgtg tctttataat tctttgatga      6780
accagatgca tttcattaac caaatccata tacatataaa tattaatcat atataattaa      6840
tatcaattgg gttagcaaaa caaatctagt ctaggtgtgt tttgcgaatg cggccgc        6897
```

<210> SEQ ID NO 14
<211> LENGTH: 253
<212> TYPE: DNA
<213> ORGANISM: Artificial
<220> FEATURE:
<223> OTHER INFORMATION: maize-wheat consensus of Figure 2

<400> SEQUENCE: 14

```
tttcatccta attaataaat aatcactggt atttgcccct ttttccaaa ttccatctga       60 ctccagatag aagaaggcta ctttctgatg tcttgcacta ccagaaagca gtccatcacg      120
catcctttct agatacactc tcaacgtcgc catgcctgct tcgaatcttc cactactcat      180
gcaactcctg ccgaatattt tcgacaatcc attaagaaaa catcccgctt tctcttccga      240
ctctcacccc atg                                                        253
```

<210> SEQ ID NO 15
<211> LENGTH: 437
<212> TYPE: DNA
<213> ORGANISM: Artificial
<220> FEATURE:
<223> OTHER INFORMATION: wheat_PRO-pIR consensus of Figure 3

<400> SEQUENCE: 15

```
tctaatcttc ttacaattat ctccataaca actgctaata actaaatcat tatcacgaat      60
gaggctaatt cttgacttct cccttgctct tctgcttctt tctcctccaa agtttgctct      120
tctctccctg tatactgatc ctcaccagat caggtcatgc atgaaaattg gctcggtatc      180
ctcctggatc actttatgct tgacctgtac atcttgcatc actatccaag caacgaaggc      240
```

```
atgcaagtcc caaattccaa aagcgccata tcccattagc tgttctgaac cgaaatacac    300
ctactcccaa acgatcacac cgacccatgc aacctccgtg cgtgtcggga taatcttgtg    360
acgctagctg actcatgcaa ctcccgtgct gtcggaatat attttcggag caaatccatt    420
aagaatttaa gatcaca                                                  437

<210> SEQ ID NO 16
<211> LENGTH: 935
<212> TYPE: DNA
<213> ORGANISM: Artificial
<220> FEATURE:
<223> OTHER INFORMATION: consensus of Figure 1

<400> SEQUENCE: 16
aagcatcggt gcttatttat acatggcaga cgcttaatag acgctctcct gtaaaaataa     60
gcacccgtgc tttagaaaaa tccggtttat ttttgtaagc acctctccta agcaccttgc    120
attgtacaag gccttggaga ataaagcag gctttcttta agtatcggtg cttatttgta    180
caggtcagac gcttaattag gcgtctctcc tgtagaaata ggcaccgatg cttcaaaaaa    240
aaacccgctc tattttttaa gcacataaca ttgtacaaga ccttaagcat ttgtcgggtg    300
cttaaaagaa agaaaagaa agaaagaatg cgatctgaaa atttaaacac tgaagggacc    360
catgtcgtcg ccctagggcc ttcctaaacg taggaccgac cctgcatgca ccgcattacg    420
ccaattatct ctccctctaa tcttcttaca attatctcca taacaactgc taataactaa    480
atcattatca cgaatgaggc tgaattcttg acttctccct tgctcttctg cttctttctc    540
ctccaaagtt tgctcttctc tccctgtata ctgatcctca ccagatcagg tcatgcatga    600
aaattggctc ggtatcctcc tggatcactt tatgcttgtt gacctgtaca tcttgcatca    660
ctatccaagc aacgaaggca tgcaagtccc aaattccaaa agcgccatat cccattagct    720
gttctgaacc gaaatacacc tactcccaaa cgatcacacc gacccatgca acctccgtgc    780
gtgtcgggat aatcttgtga cgctagctga ctcatgcaac tcccgtgcgt gtcggaatat    840
attttcggag caaatccatt aagaatttaa gatcacattg cccgcgcttt tttcgtctgc    900
atgcaaaaca gagccactgc cctctacctc catgg                              935

<210> SEQ ID NO 17
<211> LENGTH: 10000
<212> TYPE: DNA
<213> ORGANISM: Artificial
<220> FEATURE:
<223> OTHER INFORMATION: T-DNA
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (2546)..(2547)
<223> OTHER INFORMATION: n is a, c, g, or t

<400> SEQUENCE: 17
gtttacccgc caatatatcc tgtcaaacac tgatagttta aactgaaggc gggaaacgac     60
aatctgatca tgagcggaga attaagggag tcacgttatg accccgccg atgacgcggg    120 acaagccgtt ttacgtttgg aactgacaga accgcaacgt tgaaggagcc actcagcaag    180
ctggtacgat tgtaatacga ctcactatag ggcgaattga gcgctgttta aacgctcttc    240
aactggaaga gcggttacca gagctggtca cctttgtcca ccaagatgga actgcggcct    300
cgaagcttgc atgcctgcag gtcgactcta gaggatctgc accgnacact gtctggtggc    360
```

```
ataccagaca gtccggtgtg ccagatcagg gcacccttcg gttcctttgc tcctttgctt      420
ttgaaccctA actttgatcg tttattggtt tgtgttgaac ctttatgcac ctgtggaata      480
tataatctag aacaaactag ttagtccaat catttgtgtt gggcattcaa ccaccaaaat      540
tatttatagg aaaaggttaa acctatttc cctttcaatc tcccccttt tggtgattga        600 tgccaacaca aaccaaagaa aatatataag tgcagaattg aactagttg cataaggtaa      660 gtgcataggt tacttagaat taaatcaatt tatacttta cttgatatgc atggttgctt      720
tcttttattt taacattttg gaccacatt gcaccacttg ttttgttttt tgcaaatctt      780
tttggaaatt cttttgcaa agtcttttgc aaatagtcaa aggtatatga ataagattgt      840
aagaagcatt ttcaagattt gaaatttctc ccctgttc aaatgctttt cctttgacta      900
aacaaaactc cccctgaata aaattctcct cttagcttc aagagggtt taaatagata      960 tcaattggaa atatatttag atgctaattt tgaaaatata ccaattgaaa atcaacatac     1020
caatttgaaa ttaaacatac caatttaaaa aatttcaaaa agtggtggtg cggtccttt      1080 gctttgggct taatatttct cccccttgg cattaacggc caaaaacgg agactttgtg      1140 agccatttat actttctccc cattggtaaa tgaaatatga gtgaaagatt ataccaaatt     1200
tggacagtga tgcggagtga cggcgaagga taaacgatac cgttagagtg gagtggaagc     1260
cttgtcttcg ccgaagactc catttccctt tcaatctacg acttagcata gaaatacact     1320
tgaaaacaca ttagtcgtag ccacgaaaga gatatgatca aaggtataca aatgagctat     1380
gtgtgtaatg tttcaatcaa agtttcgaga atcaagaata tttagctcat tcctaagttt     1440
gctaaaggtt ttatcatcta atggtttggt aaagatatcg actaattgtt ctttggtgct     1500
aacataagca atctcgatat caccccttg ttggtgatcc ctcaaaaagt gataccgaat      1560
gtctatgtgc ttagtgcggc tgtgttcaac gggattatcc gccatgcaga tagcactctc     1620
tcattgtcac ataggagagg gacttgctc aatttgtagc catagtccct aaggttttgc      1680
ctcatccaaa gtaattgcac acaacaatgt cctgcggcaa tatacttggc ttcggcggta     1740
gaaagagcta ttgagttttg tttctttgaa gtccaagaca ccagggatct ccctagaaac     1800
tgacaagtcc ctgatgtgct cttcctatca attttacacc ctgcccaatc ggcatctgaa     1860
tatcctatta aatcaaaggt ggatcccttg gggtaccaaa tttaaggagt gtaaactaaa     1920
tatctcatga ttcttttcac ggccctaagg tgaacttcct taggatcggc ttggaatctt     1980
gcacacatgc atatagaaag catagctatc tggtcgagat gcacataaat agagtaaaga     2040
tcctatcatc gaccggtata cctttggtc gtacggattc acctcccgtg tcgaggtcga     2100
gatgcccatt agttcccatg ggtgtacctg atgggcttgg catccttcat tccaacttg      2160 ttgagtatgt cttgaatgta ctttgtttgg ctgatgaagg tgccatcttg gagttgcttg     2220
acttgaaatc ctagaaaata tttcaacttc cccatcatag acatctcgaa tttcggaatc     2280
atgatcctac taaactcttc acaagtagat ttgttagtag acccaaatat aatatcatca     2340
acataaattt ggcatacaaa caaaactttt gaaatggttt tagtaaagag agtaggatcg     2400 gcttactga ctctgaagcc attagtgata agaaaatctc ttaggcattc ataccatgct      2460
gttggggctt gcttgagccc ataaagcgcc tttgagagtt tataaacatg gttagggtac     2520
tcactatctt caaagccgag aggttnntca acatagacct attcaccca tttgatcact      2580 tttttggtcc ttcaggatct aatagttatg tataatttag agtctcttgt ttaatggcca     2640
gatatttcta attaatctaa gaatttatga tatttttaa tttttatca tgtctgatga      2700
```

```
gaattaacat aaaggctcaa ttgggtcctg aattaataat agagtgaaaa ttaatccaga      2760
ggctctatta gaaccttcaa ttagtaatac caagatatat ataagatagt agagtatagt      2820
ttaaatgttg gcattgttca ttctttcttt tgttatttaa tttatgcttt ccacggtggt      2880
tagtggttac ttctgaaggg tccaaataat gcatgaagag tttgaggaca agaagtctgc      2940
cctaaaaata gcgatgcaaa ggcatggtgt ccaagccata catatagcgc actaatttta      3000
tcagcagaac aatggtattt ataggtccta gtgcccaggc aacaagagac acgaataaag      3060
catcgatcac gacaccatgg cggcgacaat ggcagtgacg acgatggtga cgaggagcaa      3120
ggagagctgg tcgtcattgc aggtcccggc ggtggcattc ccttggaagc cacgaggtgg      3180
caagaccggc ggcctcgagt tccctcgccg ggcgatgttc gccagcgtcg gcctcaacgt      3240
gtgcccgggc gtcccggcgg ggcgcgaccc gcgggagccc gatcccaagg tcgtccgggc      3300
ggcctgcggc ctggtccagg cacaagtcct cttccagggg tttaactggg agtcgtgcaa      3360
gcagcaggga ggctggtaca acaggctcaa ggcccaggtc gacgcatcg ccaaggccgg      3420 cgtcacgcac gtctggctgc ctccaccctc gcactccgtc tcgccacaag gctacatgcc      3480
aggccgccta tacgacctgg acgcgtccaa gtacggcacg gcggcggagc tcaagtccct      3540
gatagcggcg ttccacggca ggggcgtgca gtgcgtggcg gacatcgtca tcaaccaccg      3600
gtgcgcggaa aagaaggacg cgcgcggcgt gtactgcatc ttcgagggcg ggactcccga      3660
cgaccgcctg gactgggggcc ccgggatgat ctgcagcgac gacacgcagt actcggacgg      3720
gacggggcac cgcgacacgg gcgaggggtt cgcggcggcg cccgacatcg accacctcaa      3780
cccgcgcgtg cagcgggagc tctccgcctg gctcaactgg ctcaggtccg acgccgtggg      3840
gttcgacggc tggcgcctcg acttcgccaa gggctactcg ccggccgtcg ccagaatgta      3900
cgtggagagc acggggccgc cgagcttcgt cgtcgcggag atatggaact cgctgagcta      3960
cagcggggac ggcaagccgg cgcccaacca ggaccagtgc cggcaggagc tgctggactg      4020
gacgcgggcc gtcggcgggc ccgccatggc gttcgacttc cccaccaagg gcctgctgca      4080
ggcgggcgtg caggggggagc tgtggcggct gcgcgacagc tccggcaacg cggccggcct      4140
gatcgggtgg gcgcccgaga aggccgtcac cttcgtcgac aaccatgaca ccgggtcgac      4200
gcagaagctc tggccgttcc catccgacaa ggtcatgcag ggctacgcct acatcctcac      4260
ccatccagga gtcccctgca ttttctacga ccacatgtat agactggaac ctgaagcagg      4320
agatatccac gctgtctgcc atcagggcgc ggaacggcat ccgcgccggg agcaagctgc      4380
ggatcctcgt ggcggacgcg gacgcgtacg tggccgtcgt cgacgagaag gtcatggtga      4440
agatcgggac aaggtacggc gtgagcagcg tggtcccgtc ggatttccac ccggcggcgc      4500
acggcaagga tttactgcgt ctgggagaaa gcgagcctcc gcgtcccggc ggggcgccac      4560
ctctagcagc tcagattgct cagtcttgtg ctgcattgca aacacagcag cacgacactg      4620
cataacgtct tttccttgag atctgacaaa gcagcattag tccgttgatc ggtgaagac      4680 cactcgtcag tgttgagttg aatgtttgat caataaaata cggcaatgct gtaagggttg      4740
ttttttatgc cattgataat acactgtact gttcagttgt tgaactctat ttcttagcca      4800
tgccaagtgc ttttcttatt ttgaataaca ttacagcaaa aagttgaaag acaaaaaaaa      4860 aaaccccga acagagtgct ttgggtccca agctacttta gactgtgttc ggcgttcccc      4920
ctaaatttct cccctatat ctcactcact tgtcacatca gcgttctctt tcccctatat       4980
ctccacgtcg acgcggccgc gaggaagaaa tcagttttaa gtcattgtcc ctgagatgtg      5040
cggtttggca acgatagcca ccgtaatcat agctcatagg tgcctacgtc aggttcggca      5100
```

```
gctctcgtgt catctcacat ggcatactac atgcttgttc aaccgttcgt cttgttccat    5160
cgtccaagcc ttgcctattc tgaaccaaga ggatacctac tcccaaacaa tccatcttac    5220
tcatgcaact tccatgcaaa cacgcacata gatcccccaa ccgcaccctc cttcccgtcg    5280
tttcccatct cttcctcctt tagagctacc actatataaa tcagggctca ttttctcgct    5340
cctcacaggc tcatcagcac cccggcagtg ccaccccgac tccctgcacc tgccatggag    5400
aagaggaacc tgcagtggcg gcgagggcgt gatggcatcg tgcagtaccc tcacctcttc    5460
ttcgcggccc tggcgctggc cctcctagtc gcggacccgt tcggcctcag tccgctggcc    5520
gaggtcgact accggccggt gaagcacgag ctcgcgccgt acggggaggt catgggcagc    5580
tggcccagag acaatgccag ccggctcagg cgcgggaggc tggagttcgt cggcgaggtg    5640
ttcgggccgg agtctatcga gttcgatctc cagggccgcg ggccgtacgc cggcctcgcc    5700
gacggccgcg tcgtgcggtg gatgggcgag gaggccgggt gggagacgtt cgccgtcatg    5760
aatcctgact ggtaagtgct cgatatcgct ccggcgtcca ctcgttacat gctataatat    5820
agtagtacta agatattttg atctgatttt ttgcattctt gggagaaacg tcatgcaaaa    5880
tttgttgttt cttggcaaag gtcagaagaa gtctgtgcca atggagtgaa ctcaacgacg    5940
aggaagcagc acgagaagga ggagttctgc ggccggccgc tcggcctgag gttccacggg    6000
gagaccggcg agctctacgt cgccgacgcg tactacggtc tcatggtcgt tggccagagc    6060
ggcggcgtgg cgtcctccgt cgcgagggaa gccgacgggg accccatccg gttcgcgaac    6120
gacctcgatg tgcacaggaa tggatccgta ttcttcactg acacgagcat gagatacagc    6180
agaaagtgag caaagcgacg taacaatccg gcttctcatt ttcaaacgcc tctgtattct    6240
ctgctgaaag agtagctcac cagacaagag ctgaatttgc agggaccatc tgaacatcct    6300
gttagaagga gaaggcaccg ggaggctgct caggtatgat ccagaaacaa gcggtgtcca    6360
tgtcgtgctc aaggggctgg tgttcccaaa cggcgtgcag atctcagagg accatcagtt    6420
tcttctcttc tccgagacaa caaactgcag gtaacaaaaa tactatctga cgatgctcat    6480
gattctaccg tatccatagt catgaacaca aaccacacga atctggcctt gaccaggata    6540
atgaggtact ggctggaagg cccaagagcg ggcgaggtag aggtgttcgc gaacctgccg    6600
ggcttccccg acaacgtgcg ctccaacggc aggggccagt tctgggtggc gatcgactgc    6660
tgccggacgc cggcgcagga ggtgttcgcc aagaggccgt ggctccggac cctgtacttc    6720
aagttcccgc tgtcgctcaa ggtgctcact tggaaggccg ccaggaggat gcacacggtg    6780
ctcgcgctcc tcgacggcga agggcgcgtc gtggaggtgc tcgaggaccg gggccacgag    6840
gtgatgaagc tggtgagcga ggtgcgggag gtgggccgca agctgtggat cggaaccgtg    6900
gcgcacaacc acatcgccac catcccctac cctttagagg actaaccatg atctatgctg    6960
tttcaatgcc tcctaatctg tgtacgtcta taaatgtcta atgcagtcac tggttgtaat    7020
cttgtttgtg tttggcaaat tggcataata atggacagat tcaatgggca ttggtgctgt    7080
agtcgcatca cactaattga atgggatcat gttgagctct cactttgcta caatttgctc    7140
cagcttgtac ggttgtaccc tcttgctcgt ctatagtaag ggccatctaa aaaaaactca    7200
aattagatct gcaatacaag tatgattggg ccgaatttgg attgtcacgg tccgcgacc    7260 gcgaattggg ctcggtttga tttagccgac atagtagtga ccgacccgag ccggcggcga    7320
gccaaaccga gcgacgccg ccatgatcaa agctatcgga cgatccccg ggctgcagga    7380 attcccatgg agtcaaagat tcaaatagag gacctaacag aactcgccgt aaagactggc    7440
```

```
gaacagttca tacagagtct cttacgactc aatgacaaga agaaaatctt cgtcaacatg    7500
gtggagcacg acacgcttgt ctactccaaa aatatcaaag atacagtctc agaagaccaa    7560
agggcaattg agacttttca acaaagggta atatccggaa acctcctcgg attccattgc    7620
ccagctatct gtcactttat tgtgaagata gtggaaaagg aaggtggctc ctacaaatgc    7680
catcattgcg ataaaggaaa ggccatcgtt gaagatgcct ctgccgacag tggtcccaaa    7740
gatggacccc cacccacgag gagcatcgtg gaaaaagaag acgttccaac cacgtcttca    7800
aagcaagtgg attgatgtga tatctccact gacgtaaggg atgacgcaca atcccactaa    7860
gctgaccgaa gctggccgct ctagaactag tggatctcga tgtgtagtct acgagaaggg    7920
ttaaccgtct cttcgtgaga ataaccgtgg cctaaaaata agccgatgag gataaataaa    7980
atgtggtggt acagtacttc aagaggttta ctcatcaaga ggatgctttt ccgatgagct    8040
ctagtagtac atcggacctc acatacctcc attgtggtga aatattttgt gctcatttag    8100
tgatgggtaa attttgttta tgtcactcta ggttttgaca tttcagtttt gccactctta    8160
ggttttgaca aataatttcc attccgcggc aaaagcaaaa caattttatt ttactttttac   8220
cactcttagc tttcacaatg tatcacaaat gccactctag aaattctgtt tatgccacag    8280
aatgtgaaaa aaaacactca cttatttgaa gccaaggtgt tcatggcatg gaaatgtgac    8340
ataaagtaac gttcgtgtat aagaaaaaat tgtactcctc gtaacaagag acggaaacat    8400
catgagacaa tcgcgtttgg aaggctttgc atcacctttg gatgatgcgc atgaatggag    8460
tcgtctgctt gctagccttc gcctaccgcc cactgagtcc gggcggcaac taccatcggc    8520
gaacgaccca gctgacctct accgaccgga cttgaatgcg ctaccttcgt cagcgacgat    8580
ggccgcgtac gctggcgacg tgccccccgca tgcatggcgg cacatggcga gctcagaccg    8640
tgcgtggctg gctacaaata cgtaccccgt gagtgcccta gctagaaact tacacctgca    8700
actgcgagag cgagcgtgtg agtgtagccg agtagatccc ccgggctgca ggtcgactct    8760
agaggatcca ccgtcgcca ccatggcctc ctccgagaac gtcatcaccg agttcatgcg    8820
cttcaaggtg cgcatggagg gcaccgtgaa cggccacgag ttcgagatcg agggcgaggg    8880
cgagggccgc ccctacgagg ccacaacac cgtgaagctg aaggtgacga agggcggccc    8940
cctgccctcc gcctgggaca tcctgtcccc ccagttccag tacggctcca aggtgtacgt    9000
gaagcacccc gccgacatcc ccgactacaa gaagctgtcc ttccccgagg gcttcaagtg    9060
ggagcgcgtg atgaacttcg aggacggcgg cgtggcgacc gtgacccagg actcctccct    9120
gcaggacggc tgcttcatct acaaggtgaa gttcatcggc gtgaacttcc cctccgacgg    9180
ccccgtgatg cagaagaaga ccatgggctg ggaggcctcc accgagcgcc tgtacccccg    9240
cgacggcgtg ctgaagggcg agacccacaa ggccctgaag ctgaaggacg gcggccacta    9300
cctggtggag ttcaagtcca tctacatggc caagaagccc gtgcagctgc ccggctacta    9360
ctacgtggac gccaagctgg acatcacctc ccacaacgag gactacacca tcgtggagca    9420
gtacgagcgc accgagggcc gccaccacct gttcctgtag cggcccatgg atattcgaac    9480
gcgtaggtac cacatggtta acctagactt gtccatcttc tggattggcc aacttaatta    9540
atgtatgaaa taaaggatg cacacatagt gacatgctaa tcactataat gtgggcatca    9600
aagttgtgtg ttatgtgtaa ttactagtta tctgaataaa agagaaagag atcatccata    9660
tttcttatcc taaatgaatg tcacgtgtct ttataattct ttgatgaacc agatgcattt    9720
cattaaccaa atccatatac atataaatat taatcatata taattaatat caattgggtt    9780
agcaaaacaa atctagtcta ggtgtgtttt gcgaatgcgg ccgccaccgc ggtggagctc    9840
```

```
gaattcattc cgattaatcg tggcctcttg ctcttcagga tgaagagcta tgtttaaacg    9900
tgcaagcgct actagacaat tcagtacatt aaaaacgtcc gcaatgtgtt attaagttgt    9960
ctaagcgtca atttgtttac accacaatat atcctgccac                          10000
```

MANIPULATION OF DOMINANT MALE STERILITY

CROSS-REFERENCE TO RELATED APPLICATIONS

This application is a continuation of patent application Ser. No. 14/774,272, filed Sep. 10, 2015, now U.S. Pat. No. 10,113,181, which is a 371 national stage entry of PCT patent application PCT/US14/23932, filed Mar. 12, 2014, which claims benefit of and priority to Provisional Application No. 61/788,950, filed Mar. 15, 2013, and Provisional Application No. 61/778,069, filed Mar. 12, 2013, all of which are incorporated herein by reference.

FIELD OF THE INVENTION

The present invention relates to the field of plant molecular biology, more particularly to influencing male fertility.

BACKGROUND OF THE INVENTION

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinated if pollen from one flower is transferred to the same or another flower of the same plant or a genetically identical plant. A plant is cross-pollinated if the pollen comes from a flower on a genetically different plant.

In certain species, such as *Brassica campestris*, the plant is normally self-sterile and can only be cross-pollinated. In self-pollinating species, such as soybeans and cotton, the male and female plants are anatomically juxtaposed. During natural pollination, the male reproductive organs of a given flower pollinate the female reproductive organs of the same flower.

Bread wheat (*Triticum aestivum*) is a hexaploid plant having three pairs of homologous chromosomes defining genomes A, B and D. The endosperm of wheat grain comprises 2 haploid complements from a maternal cell and 1 from a paternal cell. The embryo of wheat grain comprises one haploid complement from each of the maternal and paternal cells. Hexaploidy has been considered a significant obstacle in researching and developing useful variants of wheat. In fact, very little is known regarding how homologous genes of wheat interact, how their expression is regulated, and how the different proteins produced by homologous genes function separately or in concert.

An essential aspect of much of the work underway with genetic male sterility systems is the identification of genes influencing male fertility and promoters associated with such genes. Such genes and promoters can be used in a variety of systems to control male fertility including those described herein.

BRIEF SUMMARY OF THE INVENTION

Compositions and methods for modulating male fertility in a plant are provided. Compositions comprise nucleotide sequences, and fragments and variants thereof, which modulate male fertility. Further provided are expression cassettes comprising one or more polynucleotides, operably linked to a promoter, wherein expression of one or more polynucleotides modulates the male fertility of a plant. Various methods are provided wherein the level and/or activity of a polynucleotide that influences male fertility is modulated in a plant or plant part.

BRIEF DESCRIPTION OF THE FIGURES

FIGS. 1A and 1B. Alignment of the wheat MS45 promoter regions of the A, B, and D genomes (SEQ ID NOs: 1, 2, and 3, respectively). A consensus sequence is also provided (SEQ ID NO: 16).

FIG. 2. Alignment of wheat MS45 promoter consensus with ZmMS45 promoter region.

FIG. 3. Alignment of wheat MS45 promoter consensus with wheat promoter inverted repeat (pIR) sequence.

DETAILED DESCRIPTION

Figure 4:
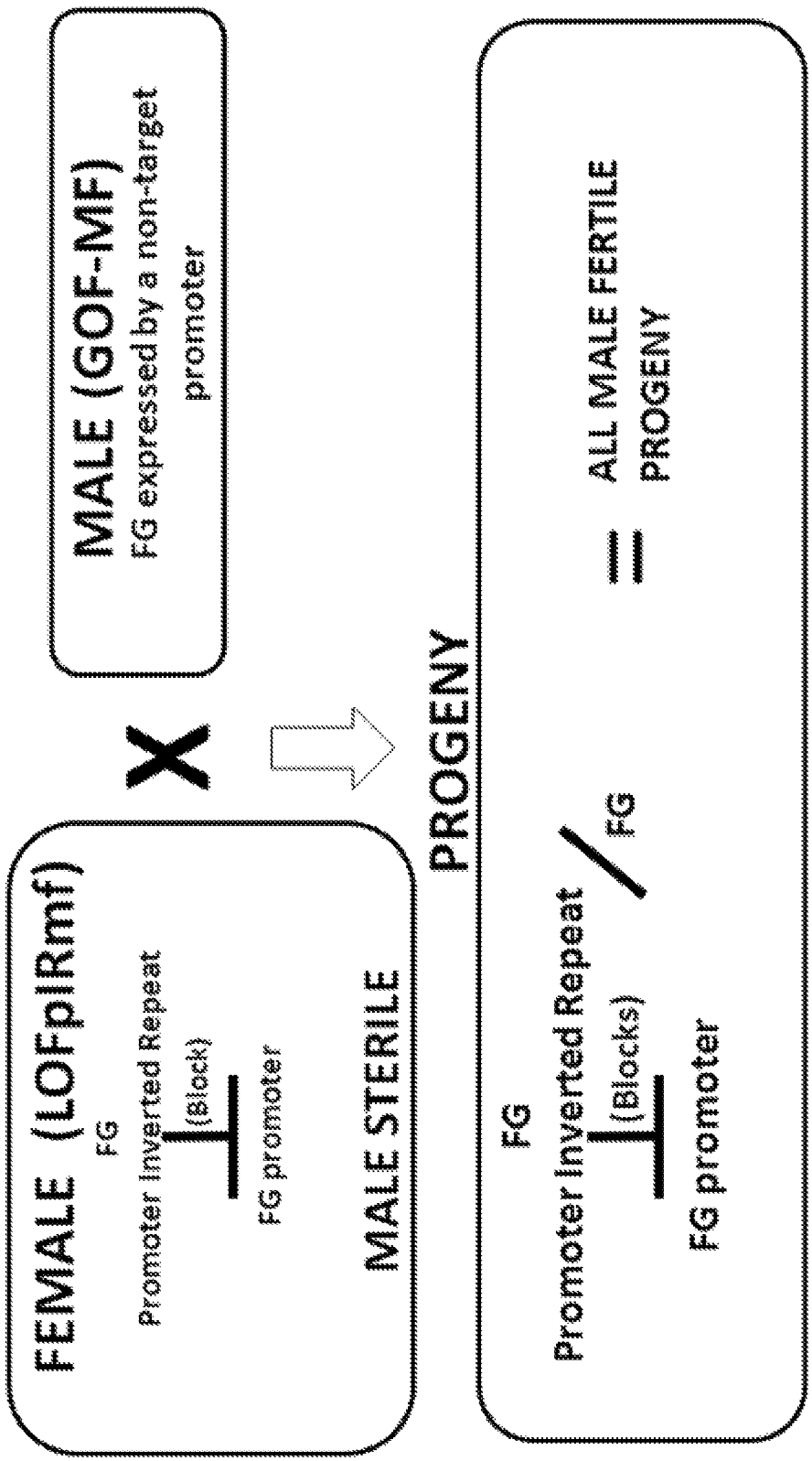
FIG. 4. Restoration of fertility by Gain of Function: GOF-MF.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Male Fertility Polynucleotides

Compositions disclosed herein include polynucleotides and polypeptides that influence male fertility. In particular, wheat MS45 promoter sequences are provided comprising nucleotide sequences set forth in SEQ ID NO: 1, 2, or 3, or fragments or variants thereof, such as SEQ ID NO: 4 or 6.

Sexually reproducing plants develop specialized tissues specific for the production of male and female gametes. Successful production of male gametes relies on proper formation of the male reproductive tissues. The stamen, which embodies the male reproductive organ of plants, contains various cell types, including for example, the filament, anther, tapetum, and pollen. As used herein, "male tissue" refers to the specialized tissue in a sexually reproducing plant that is responsible for production of the male gamete. Male tissues include, but are not limited to, the stamen, filament, anther, tapetum, and pollen.

The process of mature pollen grain formation begins with microsporogenesis, wherein meiocytes are formed in the sporogenous tissue of the anther. Microgametogenesis follows, wherein microspores divide mitotically and develop into the microgametophyte, or pollen grains. The condition of "male fertility" or "male fertile" refers to those plants producing a mature pollen grain capable of fertilizing a female gamete to produce a subsequent generation of offspring. The term "influences male fertility" or "modulates male fertility", as used herein, refers to any increase or decrease in the ability of a plant to produce a mature pollen grain when compared to an appropriate control. A "mature pollen grain" or "mature pollen" refers to any pollen grain capable of fertilizing a female gamete to produce a subsequent generation of offspring. Likewise, the term "male fertility polynucleotide" or "male fertility polypeptide" refers to a polynucleotide or polypeptide that modulates male fertility. A male fertility polynucleotide may, for example, encode a polypeptide that participates in the process of microsporogenesis or microgametogenesis.

Expression of fertility genes has been shown to influence male fertility in a variety of ways. Mutagenesis studies of Ms22 (also referred to as Msca1) resulted in phenotypically male sterile maize plants with anthers that did not extrude from the tassel and lacked sporogenous tissue. West and Albertsen (1985) Maize Newsletter 59:87; Neuffer et al. (1977) Mutants of maize. *Cold Spring Harbor Laboratory Press*, Cold Spring Harbor, N.Y. See also U.S. Pat. No. 7,919,676.

Certain male sterility genes such as MAC1, EMS1 or GNE2 (Sorensen et al. (2002) *Plant J*. 29:581-594) prevent cell growth in the quartet stage. Mutations in the SPOROCYTELESS/NOZZLE gene act early in development, but impact both anther and ovule formation such that plants are male and female sterile. The SPOROCYTELESS gene of *Arabidopsis* is required for initiation of sporogenesis and encodes a novel nuclear protein (*Genes Dev*. 1999 Aug. 15; 13(16):2108-17).

Ms26 polypeptides have been reported to have significant homology to P450 enzymes found in yeast, plants, and mammals. P450 enzymes have been widely studied and characteristic protein domains have been elucidated. The Ms26 protein contains several structural motifs characteristic of eukaryotic P450's, including the heme-binding domain FxxGxRxCxG (domain D), domain A A/GGXD/ETT/S (dioxygen-binding), domain B (steroid-binding) and domain C. Phylogenetic tree analysis revealed that Ms26 is most closely related to P450s involved in fatty acid omega-hydroxylation found in *Arabidopsis thaliana* and *Vicia sativa*. See, for example, US Patent Publication No. 2012/0005792, herein incorporated by reference.

The Ms45 polynucleotide is a male fertility polynucleotide characterized in maize (see, for example, U.S. Pat. No. 5,478,369) and wheat (U.S. provisional patent application 61/697,590 filed Sep. 6, 2012). Mutations of Ms45 can result in breakdown of microsporogenesis during vacuolation of the microspores rendering the mutated plants male sterile. When the cloned Ms45 polynucleotide is introduced into such mutated male sterile plants, the gene can complement the mutation and confer male fertility. The cloned Ms45 gene, for example the Ms45 gene of maize or wheat or rice, can also be used to complement male sterility induced by expression of pIR molecule targeting the Ms45 promoter, as described herein. Certain embodiments described herein using the MS45 gene and/or promoter could be practiced with other genes, such as MS26 or Ms22.

Strategies for manipulation of expression of male-fertility polynucleotides in wheat will require consideration of the ploidy level of the individual wheat variety. *Triticum aestivum* is a hexaploid containing three genomes designated A, B, and D (N=21); each genome comprises seven pairs of nonhomologous chromosomes. Einkorn wheat varieties are diploids (N=7) and emmer wheat varieties are tetraploids (N=14).

Isolated or substantially purified nucleic acid molecules or protein compositions are disclosed herein. An "isolated" or "purified" nucleic acid molecule, polynucleotide, or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the polypeptides disclosed herein or biologically active portion thereof is recombinantly produced, optimally culture medium represents less than about 30%, 20%, 10%, 5%, or 1% (by dry weight) of chemical precursors or non-protein-of-interest chemicals.

A "subject plant" or "subject plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or plant cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

A. Fragments and Variants of Male Fertility Sequences

Fragments and variants of the disclosed polynucleotides and proteins encoded thereby are also provided. By "fragment" is intended a portion of the polynucleotide or a portion of the amino acid sequence and hence protein encoded thereby. Fragments of a polynucleotide may encode protein fragments that retain the biological activity of the native protein and hence influence male fertility. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length polynucleotide encoding the polypeptides disclosed herein. A fragment of a promoter polynucleotide may or may not retain promoter function. A fragment of a promoter polynucleotide may be used to create a pIR (promoter inverted repeat, aka hairpin) useful in a suppression construct which targets that promoter. See, for example, Matzke, et al., (2001) Curr. Opin. Genet. Devel. 11:221-227; Mette et al., EMBO J. (2000) 19:5194-5201.

A fragment of a polynucleotide that encodes a biologically active portion of a polypeptide that influences male fertility may encode at least 15, 25, 30, 50, 100, 150, 200, 250, 300, 350, 400, 450, 500, 525, or 537 contiguous amino acids, or up to the total number of amino acids present in a full-length polypeptide that influences male fertility. Fragments of a polynucleotide encoding a polypeptide that influences male fertility that are useful as hybridization probes or PCR primers generally need not encode a biologically active portion of a polypeptide that influences male fertility.

Thus, a fragment of a male fertility polynucleotide as disclosed herein may encode a biologically active portion of a male fertility polypeptide, or it may be a fragment that can be used as a hybridization probe or PCR primer using methods disclosed below, or it may be a fragment of a promoter sequence natively associated with a male fertility polynucleotide. A biologically active portion of a male fertility polypeptide can be prepared by isolating a portion of one of the male fertility polynucleotides disclosed herein, expressing the encoded portion of the male fertility protein (e.g., by recombinant expression in vitro), and assessing the activity of the encoded portion of the male fertility polypeptide. Polynucleotides that are fragments of a male fertility polynucleotide comprise at least 16, 20, 50, 75, 100, 150, 200, 250, 300, 350, 400, 450, 500, 550, 600, 650, 700, 800, 900, 1000, 1100, 1200, 1300, 1400, 1500, 1600, or 1629 nucleotides, or up to the number of nucleotides present in a full-length male fertility polynucleotide.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the male fertility polypeptides disclosed herein. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a male fertility polypeptide. Generally, variants of a particular polynucleotide disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins disclosed herein are biologically active, that is they continue to possess the desired biological activity of the native protein, that is, male fertility activity as described herein. Such variants may result from, for example, genetic polymorphism or from human manipulation. Biologically active variants of a male fertility protein disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein disclosed herein may differ from that protein by as few as 1-15 amino acid residues, as few as 1-10, such as 6-10, as few as 5, as few as 4, 3, 2, or even 1 amino acid residue.

The proteins disclosed herein may be altered in various ways including amino acid substitutions, deletions, truncations, and insertions. Methods for such manipulations are generally known in the art. For example, amino acid sequence variants and fragments of the male fertility polypeptides can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides disclosed herein include both the naturally occurring sequences as well as DNA sequence variants which retain function. Likewise, the male fertility polypeptides and proteins encompass both naturally occurring polypeptides as well as variations and modified forms thereof. Such polynucleotide and polypeptide variants will continue to possess the desired male fertility activity. The mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying for male fertility activity.

Increases or decreases in male fertility can be assayed in a variety of ways. One of ordinary skill in the art can readily assess activity of the variant or fragment by introducing the polynucleotide into a plant homozygous for a stable male sterile allele of the polynucleotide, and observing male tissue development in the plant. In certain embodiments, the variant or fragment polynucleotide is introduced into a plant which is male-sterile as a result of expression of a polynucleotide which confers dominant male sterility. Such a polynucleotide conferring dominant male sterility may be, for example, a pIR directed to the native promoter of a fertility gene, or a polynucleotide encoding a polypeptide which interferes with development of reproductive tissue, such as DAM-methylase or barnase (See, for example, U.S. Pat. No. 5,792,853 or 5,689,049; PCT/EP89/00495).

Variant functional polynucleotides and proteins also encompass sequences and proteins derived from a mutagenic and recombinogenic procedure such as DNA shuffling. With such a procedure, one or more different male fertility sequences can be manipulated to create a new male fertility polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the male fertility polynucleotides disclosed herein and other known male fertility polynucleotides to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

II. Sequence Analysis

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The use of the term "polynucleotide" is not intended to limit the present disclosure to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides disclosed herein also encompass all forms of sequences including, but not limited to, single-stranded forms, double-stranded forms, hairpins, stem-and-loop structures, and the like.

III. Expression Cassettes

The male fertility polynucleotides disclosed herein can be provided in expression cassettes for expression in an organism of interest. The cassette can include 5' and 3' regulatory sequences operably linked to a male fertility polynucleotide as disclosed herein. "Operably linked" is intended to mean a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame.

The expression cassettes disclosed herein may include in the 5'-3' direction of transcription, a transcriptional and translational initiation region (i.e., a promoter), a polynucleotide of interest, and a transcriptional and translational termination region (i.e., termination region) functional in the host cell (i.e., the plant). Expression cassettes are also provided with a plurality of restriction sites and/or recombination sites for insertion of the male fertility polynucleotide to be under the transcriptional regulation of the regulatory regions described elsewhere herein. The regulatory regions (i.e., promoters, transcriptional regulatory regions, and translational termination regions) and/or the polynucleotide of interest may be native/analogous to the host cell or to each other. Alternatively, the regulatory regions and/or the polynucleotide of interest may be heterologous to the host cell or to each other. As used herein, "heterologous" in reference to a polynucleotide or polypeptide sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric polynucleotide comprises a coding sequence operably linked to a transcription initiation region that is heterologous to the coding sequence.

In certain embodiments the polynucleotides disclosed herein can be stacked with any combination of polynucleotide sequences of interest or expression cassettes as disclosed elsewhere herein. For example, the male fertility polynucleotides disclosed herein may be stacked with any other polynucleotides encoding male-gamete disruptive polynucleotides or polypeptides, cytotoxins, markers, or other male fertility sequences as disclosed elsewhere herein. The stacked polynucleotides may be operably linked to the same promoter as the male fertility polynucleotide, or may be operably linked to a separate promoter polynucleotide.

As described elsewhere herein, expression cassettes may comprise a promoter operably linked to a polynucleotide of interest, along with a corresponding termination region. The termination region may be native to the transcriptional initiation region, may be native to the operably linked male fertility polynucleotide of interest or with the male fertility promoter sequences, may be native to the plant host, or may be derived from another source (i.e., foreign or heterologous). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides of interest may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Johnson et al. (1986) *Virology* 154:9-20), and human immunoglobulin heavy-chain binding protein (BiP) (Macej ak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A. Expression Cassettes Comprising a Male Fertility Polynucleotide

In particular embodiments, the expression cassettes disclosed herein comprise a promoter operably linked to a male fertility polynucleotide, or active fragment or variant thereof, as disclosed herein. In certain embodiments, a male fertility promoter disclosed herein, or an active fragment or variant thereof, is operably linked to a male fertility polynucleotide disclosed herein, or an active fragment or variant thereof.

In certain embodiments, plant promoters can preferentially initiate transcription in certain tissues, such as stamen, anther, filament, and pollen, or developmental growth stages, such as sporogenous tissue, microspores, and microgametophyte. Such plant promoters are referred to as "tissue-preferred", "cell type-preferred", or "growth-stage preferred". Promoters which initiate transcription only in certain tissue are referred to as "tissue-specific". Likewise, promoters which initiate transcription only at certain growth stages are referred to as "growth stage-specific". A "cell type-specific" promoter drives expression only in certain cell types in one or more organs, for example, stamen cells, or individual cell types within the stamen such as anther, filament, or pollen cells.

Male fertility polynucleotides disclosed herein, and active fragments and variants thereof, can be operably linked to male-tissue-specific or male-tissue-preferred promoters including, for example, stamen-specific or stamen-preferred promoters, anther-specific or anther-preferred promoters, pollen-specific or pollen-preferred promoters, tapetum-specific promoters or tapetum-preferred promoters, and the like. Promoters can be selected based on the desired outcome. For example, the polynucleotides of interest can be operably linked to constitutive, tissue-preferred, growth stage-preferred, or other promoters for expression in plants.

In one embodiment, the promoters may be those which preferentially express a polynucleotide of interest in the male tissues of the plant. No particular male fertility tissue-preferred promoter must be used in the process, and any of the many such promoters known to one skilled in the art may be employed. One such promoter is the 5126 promoter, which preferentially directs expression of the polynucleotide to which it is linked to male tissue of the plants, as described in U.S. Pat. Nos. 5,837,851 and 5,689,051. Other examples include the maize Ms45 promoter described at U.S. Pat. No. 6,037,523; SF3 promoter described at U.S. Pat. No. 6,452,069; the BS92-7 promoter described at WO 02/063021; a SGB6 regulatory element described at U.S. Pat. No. 5,470,359; the TA29 promoter (Koltunow, et al., (1990) Plant Cell 2:1201-1224; Goldberg, et al., (1993) Plant Cell 5:1217-1229 and U.S. Pat. No. 6,399,856); the type 2 metallothionein-like gene promoter (Charbonnel-Campaa, et al., Gene (2000) 254:199-208) and the *Brassica* Bca9 promoter (Lee, et al., (2003) Plant Cell Rep. 22:268-273).

In some embodiments, expression cassettes comprise male-gamete-preferred promoters operably linked to a male fertility polynucleotide. Male-gamete-preferred promoters include the PG47 promoter (U.S. Pat. Nos. 5,412,085; 5,545,546; *Plant J* 3(2):261-271 (1993)), as well as ZM13 promoter (Hamilton, et al., (1998) Plant Mol. Biol. 38:663-669); actin depolymerizing factor promoters (such as Zmabp1, Zmabp2; see, for example Lopez, et al., (1996) Proc. Natl. Acad. Sci. USA 93:7415-7420); the promoter of the maize pectin methylesterase-like gene, ZmC5 (Wakeley, et al., (1998) Plant Mol. Biol. 37:187-192); the profilin gene promoter Zmprol (Kovar, et al., (2000) The Plant Cell 12:583-598); the sulphated pentapeptide phytosulphokine gene ZmPSK1 (Lorbiecke, et al., (2005) Journal of Experimental Botany 56(417):1805-1819); the promoter of the calmodulin binding protein Mpcbp (Reddy, et al., (2000) J. Biol. Chem. 275(45):35457-70).

As disclosed herein, constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) *Plant Cell* 2:163-171); ubiquitin (Christensen et al. (1989) *Plant Mot. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

"Seed-preferred" promoters include both those promoters active during seed development such as promoters of seed storage proteins as well as those promoters active during seed germination. See Thompson et al. (1989) *BioEssays* 10:108, herein incorporated by reference. Such seed-preferred promoters include, but are not limited to, Ciml (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also WO 00/12733, where seed-preferred promoters from end1 and end2 genes are disclosed; herein incorporated by reference. Additional embryo specific promoters are disclosed in Sato et al. (1996) *Proc. Natl. Acad. Sci.* 93:8117-8122; Nakase et al. (1997) *Plant J* 12:235-46; and Postma-Haarsma et al. (1999) *Plant Mol. Biol.* 39:257-71. Additional endosperm specific promoters are disclosed in Albani et al. (1984) *EMBO* 3:1405-15; Albani et al. (1999) *Theor. Appl. Gen.* 98:1253-62; Albani et al. (1993) *Plant J.* 4:343-55; Mena et al. (1998) *The Plant Journal* 116:53-62, and Wu et al. (1998) *Plant Cell Physiology* 39:885-889.

Dividing cell or meristematic tissue-preferred promoters have been disclosed in Ito et al. (1994) *Plant Mol. Biol.* 24:863-878; Reyad et al. (1995) *Mo. Gen. Genet.* 248:703-711; Shaul et al. (1996) *Proc. Natl. Acad. Sci.* 93:4868-4872; Ito et al. (1997) *Plant J.* 11:983-992; and Trehin et al. (1997) *Plant Mol. Biol.* 35:667-672.

Stress inducible promoters include salt/water stress-inducible promoters such as P5CS (Zang et al. (1997) *Plant Sciences* 129:81-89); cold-inducible promoters, such as, cor15a (Hajela et al. (1990) *Plant Physiol.* 93:1246-1252), cor15b (Wlihelm et al. (1993) *Plant Mot Biol* 23:1073-1077), wsc120 (Ouellet et al. (1998) *FEBS Lett.* 423-324-328), ci7 (Kirch et al. (1997) *Plant Mol Biol.* 33:897-909), ci21A (Schneider et al. (1997) *Plant Physiol.* 113:335-45); drought-inducible promoters, such as, Trg-31 (Chaudhary et al (1996) *Plant Mol. Biol.* 30:1247-57), rd29 (Kasuga et al. (1999) *Nature Biotechnology* 18:287-291); osmotic inducible promoters, such as, Rab17 (Vilardell et al. (1991) *Plant Mol. Biol.* 17:985-93) and osmotin (Raghothama et al. (1993) *Plant Mol Biol* 23:1117-28); and, heat inducible promoters, such as, heat shock proteins (Barros et al. (1992) *Plant Mol.* 19:665-75; Marrs et al. (1993) *Dev. Genet.* 14:27-41), and smHSP (Waters et al. (1996) *J. Experimental Botany* 47:325-338). Other stress-inducible promoters include rip2 (U.S. Pat. No. 5,332,808 and U.S. Publication No. 2003/0217393) and rp29a (Yamaguchi-Shinozaki et al. (1993) *Mol. Gen. Genetics* 236:331-340).

As discussed elsewhere herein, the expression cassettes comprising male fertility polynucleotides may be stacked with other polynucleotides of interest. Any polynucleotide of interest may be stacked with the male fertility polynucleotide, including for example, male-gamete-disruptive polynucleotides and marker polynucleotides.

Male fertility polynucleotides disclosed herein may be stacked in or with expression cassettes comprising a promoter operably linked to a polynucleotide which is male-gamete-disruptive; that is, a polynucleotide which interferes with the function, formation, or dispersal of male gametes. A male-gamete-disruptive polynucleotide can operate to prevent function, formation, or dispersal of male gametes by any of a variety of methods. By way of example but not limitation, this can include use of polynucleotides which encode a gene product such as DAM-methylase or barnase (See, for example, U.S. Pat. No. 5,792,853 or 5,689,049; PCT/EP89/00495); encode a gene product which interferes with the accumulation of starch or affects osmotic balance in pollen (See, for example, U.S. Pat. Nos. 7,875,764; 8,013,218; 7,696,405); inhibit formation of a gene product important to male gamete function, formation, or dispersal (See, for example, U.S. Pat. Nos. 5,859,341; 6,297,426); encode a gene product which combines with another gene product to prevent male gamete formation or function (See U.S. Pat. Nos. 6,162,964; 6,013,859; 6,281,348; 6,399,856; 6,248,935; 6,750,868; 5,792,853); are antisense to, or cause cosuppression of, a gene critical to male gamete function, formation, or dispersal (See U.S. Pat. Nos. 6,184,439; 5,728,926; 6,191,343; 5,728,558; 5,741,684); interfere with expression of a male fertility polynucleotide through use of hairpin formations (Smith et al. (2000) *Nature* 407:319-320; WO 99/53050 and WO 98/53083; Matzke, et al., (2001) *Curr. Opin. Genet. Devel.* 11:221-227); see also Scheid, et al., (2002) *Proc. Natl. Acad. Sci., USA* 99:13659-13662; Waterhouse and Helliwell, (2003) *Nature Reviews Genetics* 4:29-38; Aufsaftz, et al., (2002) *Proc. Nat'l. Acad. Sci.* 99(4):16499-16506; Sijen, et al., (2001) *Curr. Biol.* 11:436-440 or the like.

Male-gamete-disruptive polynucleotides include dominant negative genes such as methylase genes and growth-inhibiting genes. See, U.S. Pat. No. 6,399,856. Dominant negative genes include diphtheria toxin A-chain gene (Czako and An (1991) Plant Physiol. 95 687-692; Greenfield et al. (1983) PNAS 80:6853); cell cycle division mutants such as CDC in maize (Colasanti et al. (1991) PNAS 88:3377-3381); the WT gene (Farmer et al. (1994) Mol. Genet. 3:723-728); and P68 (Chen et al. (1991) PNAS 88:315-319).

Further examples of male-gamete-disruptive polynucleotides include, but are not limited to, pectate lyase gene pelE from *Erwinia chrysanthermi* (Kenn et al (1986) J. Bacteriol. 168:595); CytA toxin gene from *Bacillus thuringiensis* Israeliensis (McLean et al (1987) J. Bacteriol. 169:1017 (1987), U.S. Pat. No. 4,918,006); DNAses, RNAses, proteases, or polynucleotides expressing anti-sense RNA. A male-gamete-disruptive polynucleotide may encode a protein involved in inhibiting pollen-stigma interactions, pollen tube growth, fertilization, or a combination thereof.

Male fertility polynucleotides disclosed herein may be stacked with expression cassettes disclosed herein comprising a promoter operably linked to a polynucleotide of interest encoding a reporter or marker product. Examples of suitable reporter polynucleotides known in the art can be found in, for example, Jefferson et al. (1991) in Plant Molecular Biology Manual, ed. Gelvin et al. (Kluwer Academic Publishers), pp. 1-33; DeWet et al. Mol. Cell. Biol. 7:725-737 (1987); Goff et al. EMBO J. 9:2517-2522 (1990); Kain et al. BioTechniques 19:650-655 (1995); and Chiu et al. Current Biology 6:325-330 (1996). In certain embodiments, the polynucleotide of interest encodes a selectable reporter. These can include polynucleotides that confer antibiotic resistance or resistance to herbicides. Examples of suitable selectable marker polynucleotides include, but are not limited to, genes encoding resistance to chloramphenicol, methotrexate, hygromycin, streptomycin, spectinomycin, bleomycin, sulfonamide, bromoxynil, glyphosate, and phosphinothricin.

In some embodiments, the expression cassettes disclosed herein comprise a polynucleotide of interest encoding scorable or screenable markers, where presence of the polynucleotide produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase, and alkaline phosphatase. Other screenable markers include the anthocyanin/flavonoid polynucleotides including, for example, a R-locus polynucleotide, which encodes a product that regulates the production of anthocyanin pigments (red color) in plant tissues, the genes which control biosynthesis of flavonoid pigments, such as the maize C1 and C2, the B gene, the p1 gene, and the bronze locus genes, among others. Further examples of suitable markers encoded by polynucleotides of interest include the cyan fluorescent protein (CYP) gene, the yellow fluorescent protein gene, a lux gene, which encodes a luciferase, the presence of which may be detected using, for example, X-ray film, scintillation counting, fluorescent spectrophotometry, low-light video cameras, photon counting cameras or multiwell luminometry, a green fluorescent protein (GFP), and DsRed2 (*Clontechniques,* 2001) where plant cells transformed with the marker gene are red in color, and thus visually selectable. Additional examples include a p-lactamase gene encoding an enzyme for which various chromogenic substrates are known (e.g., PADAC, a chromogenic cephalosporin), a xylE gene encoding a catechol dioxygenase that can convert chromogenic catechols, an α-amylase gene, and a tyrosinase gene encoding an enzyme capable of oxidizing tyrosine to DOPA and dopaquinone, which in turn condenses to form the easily detectable compound melanin.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J Cell Science* 117:943-54 and Kato et al. (2002) *Plant Physiol* 129:913-42), and yellow florescent protein (PhiYFP™ from Evrogen, see, Bolte et al. (2004) 1 Cell Science 117: 943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the compositions and methods disclosed herein.

In some embodiments, the expression cassettes disclosed herein comprise a first polynucleotide of interest encoding a male fertility polynucleotide operably linked to a first promoter polynucleotide, stacked with a second polynucleotide of interest encoding a male-gamete-disruptive gene product operably linked to a male tissue-preferred promoter polynucleotide. In other embodiments, the expression cassettes described herein may also be stacked with a third polynucleotide of interest encoding a marker polynucleotide operably linked to a third promoter polynucleotide.

In specific embodiments, the expression cassettes disclosed herein comprise a first polynucleotide of interest encoding a wheat male fertility gene disclosed herein operably linked to a promoter, which may be a tissue-preferred or constitutive promoter, such as the cauliflower mosaic virus (CaMV) 35S promoter. The expression cassettes may further comprise a second polynucleotide of interest encoding a male-gamete-disruptive gene product operably linked to a male tissue-preferred promoter. In certain embodiments, the expression cassettes disclosed herein may further comprise a third polynucleotide of interest encoding a marker gene, such as the phosphinothricin acetyltransferase (PAT) gene from *Streptomyces viridochomagenes* operably linked to a constitutive promoter, such as the cauliflower mosaic virus (CaMV) 35S promoter.

IV. Plants

A. Plants Having Altered Levels/Activity of Male Fertility Polypeptide

Further provided are plants having altered levels and/or activities of a male fertility polypeptide and/or altered levels of male fertility. In some embodiments, the plants disclosed herein have stably incorporated into their genomes a heterologous male fertility polynucleotide, or active fragments or variants thereof, as disclosed herein. Thus, plants, plant cells, plant parts, and seeds are provided which comprise at least one heterologous male fertility polynucleotide as set forth in any one of SEQ ID NO: 1, 2, 3, 4, 5, 6, 7, 8, 9, 10, 11, 12, or 13, or any useful fragments or variants disclosed herein.

Plants are further provided comprising the expression cassettes disclosed herein comprising a male fertility polynucleotide operably linked to a promoter that is active in the plant. In some embodiments, expression of the male fertility polynucleotide modulates male fertility of the plant. In certain embodiments, expression of the male fertility polynucleotide increases male fertility of the plant. For example, plants are provided comprising an expression cassette comprising an MS45 polynucleotide as set forth in SEQ ID NO: 8, or an active fragment or variant thereof, operably linked to a promoter. Upon expression of the Ms45 polynucleotide, male fertility of the plant is increased.

In certain embodiments, expression cassettes comprising a heterologous male fertility polynucleotide as disclosed herein, or an active fragment or variant thereof, operably linked to a promoter active in a plant, are provided to a male sterile plant. Upon expression of the heterologous male fertility polynucleotide, the male fertility of the plant is restored. In specific embodiments, the plants disclosed herein comprise an expression cassette comprising a heterologous male fertility polynucleotide as disclosed herein, or an active fragment or variant thereof, operably linked to a promoter, stacked with one or more expression cassettes comprising a polynucleotide of interest operably linked to a promoter active in the plant. For example, the stacked polynucleotide of interest can comprise a male-gamete-disruptive polynucleotide and/or a marker polynucleotide.

Plants disclosed herein may also comprise stacked expression cassettes described herein comprising at least two polynucleotides such that the at least two polynucleotides are inherited together in more than 50% of meioses, i.e., not randomly. Accordingly, when a plant or plant cell comprising stacked expression cassettes with two polynucleotides undergoes meiosis, the two polynucleotides segregate into the same progeny (daughter) cell. In this manner, stacked polynucleotides will likely be expressed together in any cell for which they are present. For example, a plant may comprise an expression cassette comprising a male fertility polynucleotide stacked with an expression cassette comprising a male-gamete-disruptive polynucleotide such that the male fertility polynucleotide and the male-gamete-disruptive polynucleotide are inherited together. Specifically, a male sterile plant could comprise an expression cassette comprising a male fertility polynucleotide disclosed herein operably linked to a constitutive promoter, stacked with an expression cassette comprising a male-gamete-disruptive polynucleotide operably linked to a male tissue-preferred promoter, such that the plant produces mature pollen grains. However, in such a plant, development of the daughter pollen cells comprising the male fertility polynucleotide will be impacted by expression of the male-gamete-disruptive polynucleotide.

B. Plants and Methods of Introduction

As used herein, the term plant includes plant cells, plant protoplasts, plant cell tissue cultures from which a plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, grain and the like. As used herein "grain" is intended the mature seed produced by commercial growers for purposes other than growing or reproducing the species. Progeny, variants, and mutants of the regenerated plants are also included within the scope of the disclosure, provided that these parts comprise the introduced nucleic acid sequences.

The methods disclosed herein comprise introducing a polypeptide or polynucleotide into a plant cell. "Introducing" is intended to mean presenting to the plant the polynucleotide or polypeptide in such a manner that the sequence gains access to the interior of a cell. The methods disclosed herein do not depend on a particular method for introducing a sequence into the host cell, only that the polynucleotide or polypeptides gains access to the interior of at least one cell of the host. Methods for introducing polynucleotide or polypeptides into host cells (i.e., plants) are known in the art and include, but are not limited to, stable transformation methods, transient transformation methods, and virus-mediated methods. In some embodiments, a polynucleotide is introduced to a plant by sexual cross to another plant. For example, pollen comprising a polynucleotide of interest is transferred to the stigma of a receptor plant, to produce progeny comprising the polynucleotide of interest.

"Stable transformation" is intended to mean that the nucleotide construct introduced into a host (i.e., a plant) integrates into the genome of the plant and is capable of being inherited by the progeny thereof "Transient transformation" is intended to mean that a polynucleotide is introduced into the host (i.e., a plant) and expressed temporally or a polypeptide is introduced into a host (i.e., a plant).

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.*

3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (*Longman*, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Wheat transformation protocols are available to one of skill in the art. See, for example, He et al. (2010) *J. Exp. Botany* 61(6):1567-1581; Wu et al. (2008) *Transgenic Res.* 17:425-436; Nehra et al. (1994) *Plant J.* 5(2):285-297; Rasco-Gaunt et al. (2001) *Exp. Botany* 52(357):865-874; Razzaq et al. (2011) *African J. Biotech.* 10(5):740-750. See also Tamas-Nyitrai, et al. (2012) *Biolistic-and Agrobacterium Mediated Transformation Protocols for Wheat* in Plant Cell Culture Protocols, Methods in Molecular Biology 877: 357-384.

In specific embodiments, the male fertility polynucleotides or expression cassettes disclosed herein can be provided to a plant using a variety of transient transformation methods. Such transient transformation methods include, but are not limited to, the introduction of the male fertility polypeptide or variants and fragments thereof directly into the plant or the introduction of a male fertility transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the male fertility polynucleotide or expression cassettes disclosed herein can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma # P3143).

In other embodiments, the male fertility polynucleotides or expression cassettes disclosed herein may be introduced into plants by contacting plants with a virus or viral nucleic acids. Generally, such methods involve incorporating a nucleotide construct of disclosed herein within a viral DNA or RNA molecule. It is recognized that a male fertility sequence disclosed herein may be initially synthesized as part of a viral polyprotein, which later may be processed by proteolysis in vivo or in vitro to produce the desired recombinant protein. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide disclosed herein can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. These are referred to as T0 plants. See, for example, McCormick et al. (1986) *Plant Cell Reports* 5:81-84. These plants may then be grown, and pollinated with either the same transformed strain or different strains, and the resulting progeny having desired expression of the desired phenotypic characteristic identified. Two or more generations (e.g. T1, T2, T3) may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a male fertility polynucleotide disclosed herein, for example, an expression cassette disclosed herein, stably incorporated into their genome. Seed comprising any expression cassette disclosed herein can be sorted based on size parameters, including but not limited to, seed length, seed width, seed density, seed color, or any combination thereof.

The male fertility polynucleotides and expression cassettes disclosed herein may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), alfalfa (*Medicago sativa*), rice (*Oryza sativa*), rye (*Secale cereale*), sorghum (*Sorghum* bicolor, Sorghum vulgare), millet (e.g., pearl millet (Pennisetum glaucum), proso millet (Panicum miliaceum), foxtail millet (Setaria italica), finger millet (Eleusine coracana)), sunflower (Helianthus annuus), safflower (Carthamus tinctorius), wheat (Triticum aestivum), soybean (Glycine max), tobacco (Nicotiana tabacum), potato (Solanum tuberosum), peanuts (Arachis hypogaea), cotton (Gossypium barbadense, Gossypium hirsutum), sweet potato (Ipomoea batatus), cassava (Manihot esculenta), coffee (Coffea spp.), coconut (Cocos mucifera), pineapple (Ananas comosus), citrus trees (Citrus spp.), cocoa (Theobroma cacao), tea (Camellia sinensis), banana (Musa spp.), avocado (Persea americana), fig (Ficus casica), guava (Psidium guajava), mango (Mangifera indica), olive (Olea europaea), papaya (Carica papaya), cashew (Anacardium occidentals), macadamia (Macadamia integrifolia), almond (Prunus amygdalus), sugar beets (Beta vulgaris), sugarcane (Saccharum spp.), oats, barley, vegetables, ornamentals, grasses and conifers.

In particular embodiments, wheat plants are used in the methods and compositions disclosed herein. As used herein, the term "wheat" refers to any species of the genus Triticum, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes T. aestivum, T. spelta, T. mocha, T. compactum, T. sphaerococcum, T. vavilovii, and interspecies cross thereof. Tetraploid wheat includes T. durum (also referred to as durum wheat or Triticum turgidum ssp. durum), T. dicoccoides, T. dicoccum, T. polonicum, and interspecies cross thereof. In addition, the term "wheat" includes possible progenitors of hexaploid or tetraploid Triticum sp. such as T. uartu, T. monococcum or T. boeoticum for the A genome, Aegilops speltoides for the B genome, and T. tauschii (also known as Aegilops squarrosa or Aegilops tauschii) for the D genome. A wheat cultivar for use in the present disclosure may belong to, but is not limited to, any of the above-listed species. Also encompassed are plants that are produced by conventional techniques using Triticum sp. as a parent in a sexual cross with a non-Triticum species, such as rye Secale cereale, including but not limited to Triticale. In some embodiments, the wheat plant is suitable for commercial production of grain, such as commercial varieties of hexaploid wheat or durum wheat, having suitable agronomic characteristics which are known to those skilled in the art.

Vegetables include tomatoes (Lycopersicon esculentum), lettuce (e.g., Lactuca sativa), green beans (Phaseolus vulgaris), lima beans (Phaseolus limensis), peas (Lathyrus spp.), and members of the genus Cucumis such as cucumber (C. sativus), cantaloupe (C. cantalupensis), and musk melon (C. melo). Ornamentals include azalea (Rhododendron spp.), hydrangea (Macrophylla hydrangea), hibiscus (Hibiscus rosasanensis), roses (Rosa spp.), tulips (Tulipa spp.), daffodils (Narcissus spp.), petunias (Petunia hybrida), carnation (Dianthus caryophyllus), poinsettia (Euphorbia pulcherrima), and chrysanthemum.

Conifers that may be employed in practicing the present methods and compositions include, for example, pines such as loblolly pine (Pinus taeda), slash pine (Pinus elliotii), ponderosa pine (Pinus ponderosa), lodgepole pine (Pinus contorta), and Monterey pine (Pinus radiata); Douglas-fir (Pseudotsuga menziesii); Western hemlock (Tsuga canadensis); Sitka spruce (Picea glauca); redwood (Sequoia sempervirens); true firs such as silver fir (Abies amabilis) and balsam fir (Abies balsamea); and cedars such as Western red cedar (Thuja plicata) and Alaska yellow-cedar (Chamaecyparis nootkatensis). In specific embodiments, plants disclosed herein are crop plants (for example, corn, alfalfa, sunflower, Brassica, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Typically, an intermediate host cell will be used in the practice of the methods and compositions disclosed herein to increase the copy number of the cloning vector. With an increased copy number, the vector containing the nucleic acid of interest can be isolated in significant quantities for introduction into the desired plant cells. In one embodiment, plant promoters that do not cause expression of the polypeptide in bacteria are employed.

Prokaryotes most frequently are represented by various strains of E. coli; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) Nature 198:1056), the tryptophan (trp) promoter system (Goeddel et al. (1980) Nucleic Acids Res. 8:4057) and the lambda derived P L promoter and N-gene ribosome binding site (Shimatake et al. (1981) Nature 292:128). The inclusion of selection markers in DNA vectors transfected in E coli, is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein disclosed herein are available using Bacillus sp. and Salmonella (Palva et al. (1983) Gene 22:229-235); Mosbach et al. (1983) Nature 302:543-545).

In some embodiments, the expression cassette or male fertility polynucleotides disclosed herein are maintained in a hemizygous state in a plant. Hemizygosity is a genetic condition existing when there is only one copy of a gene (or set of genes) with no allelic counterpart on the sister chromosome. In certain embodiments, the expression cassettes disclosed herein comprise a first promoter operably linked to a male fertility polynucleotide which is stacked with a male-gamete-disruptive polynucleotide operably linked to a male tissue-preferred promoter, and such expression cassettes are introduced into a male sterile plant in a hemizygous condition. When the male fertility polynucleotide is expressed, the plant is able to successfully produce mature pollen grains because the male fertility polynucleotide restores the plant to a fertile condition. Given the hemizygous condition of the expression cassette, only certain daughter cells will inherit the expression cassette in the process of pollen grain formation. The daughter cells that inherit the expression cassette containing the male fertility polynucleotide will not develop into mature pollen grains due to the male tissue-preferred expression of the stacked encoded male-gamete-disruptive gene product. Those pollen grains that do not inherit the expression cassette will continue to develop into mature pollen grains and be functional, but will not contain the male fertility polynucleotide of the expression cassette and therefore will not transmit the male fertility polynucleotide to progeny through pollen.

V. Modulating the Concentration and/or Activity of Male Fertility Polypeptides

A method for modulating the concentration and/or activity of the male fertility polypeptides disclosed herein in a plant is provided. The term "influences" or "modulates", as used herein with reference to the concentration and/or activity of the male fertility polypeptides, refers to any increase or decrease in the concentration and/or activity of the male fertility polypeptides when compared to an appropriate control. In general, concentration and/or activity of a male fertility polypeptide disclosed herein is increased or decreased by at least 1%, 5%, 10%, 20%, 30%, 40%, 50%, 60%, 70%, 80%, or 90% relative to a native control plant, plant part, or cell. Modulation as disclosed herein may occur during and/or subsequent to growth of the plant to the desired stage of development. In specific embodiments, the male fertility polypeptides disclosed herein are modulated in monocots, particularly wheat.

A variety of methods can be employed to assay for modulation in the concentration and/or activity of a male fertility polypeptide. For instance, the expression level of the male fertility polypeptide may be measured directly, for example, by assaying for the level of the male fertility polypeptide or RNA in the plant (i.e., Western or Northern blot), or indirectly, for example, by assaying the male fertility activity of the male fertility polypeptide in the plant. Methods for measuring the male fertility activity are described elsewhere herein. In specific embodiments, modulation of male fertility polypeptide concentration and/or activity comprises the modulation (i.e., an increase or a decrease) in the level of male fertility polypeptide in the plant. Methods to measure the level and/or activity of male fertility polypeptides are known in the art and are discussed elsewhere herein. In still other embodiments, the level and/or activity of the male fertility polypeptide is modulated in vegetative tissue, in reproductive tissue, or in both vegetative and reproductive tissue.

In one embodiment, the activity and/or concentration of the male fertility polypeptide is increased by introducing the polypeptide or the corresponding male fertility polynucleotide into the plant. Subsequently, a plant having the introduced male fertility sequence is selected using methods known to those of skill in the art such as, but not limited to, Southern blot analysis, DNA sequencing, PCR analysis, or phenotypic analysis. In certain embodiments, marker polynucleotides are introduced with the male fertility polynucleotide to aid in selection of a plant having or lacking the male fertility polynucleotide disclosed herein. A plant or plant part altered or modified by the foregoing embodiments is grown under plant forming conditions for a time sufficient to modulate the concentration and/or activity of the male fertility polypeptide in the plant. Plant forming conditions are well known in the art.

As discussed elsewhere herein, many methods are known the art for providing a polypeptide to a plant including, but not limited to, direct introduction of the polypeptide into the plant, or introducing into the plant (transiently or stably) a polynucleotide construct encoding a male fertility polypeptide. It is also recognized that the methods disclosed herein may employ a polynucleotide that is not capable of directing, in the transformed plant, the expression of a protein or an RNA. Thus, the level and/or activity of a male fertility polypeptide may be increased by altering the gene encoding the male fertility polypeptide or its promoter. See, e.g., Kmiec, U.S. Pat. No. 5,565,350; Zarling et al., PCT/US93/03868. Therefore mutagenized plants that carry mutations in male fertility genes, where the mutations increase expression of the male fertility gene or increase the activity of the encoded male fertility polypeptide are provided.

In other embodiments, the concentration and/or activity of a male fertility polypeptide is increased by introduction into a plant of an expression cassette comprising a male fertility polynucleotide (e.g. SEQ ID NO: 8 or 10), or an active fragment or variant thereof, as disclosed elsewhere herein. The male fertility polynucleotide may be operably linked to promoter that is heterologous to the plant or native to the plant. By increasing the concentration and/or activity of a male fertility polypeptide in a plant, the male fertility of the plant is likewise increased. Thus, the male fertility of a plant can be increased by increasing the concentration and/or activity of a male fertility polypeptide. For example, male fertility can be restored to a male sterile plant by increasing the concentration and/or activity of a male fertility polypeptide.

It is also recognized that the level and/or activity of the polypeptide may be modulated by employing a polynucleotide that is not capable of directing, in a transformed plant, the expression of a protein or an RNA. For example, the polynucleotides disclosed herein may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference. It is therefore recognized that methods disclosed herein do not depend on the incorporation of the entire polynucleotide into the genome, only that the plant or cell thereof is altered as a result of the introduction of the polynucleotide into a cell.

In one embodiment, the genome may be altered following the introduction of the polynucleotide into a cell. For example, the polynucleotide, or any part thereof, may incorporate into the genome of the plant. Alterations to the genome disclosed herein include, but are not limited to, additions, deletions, and substitutions of nucleotides into the genome. While the methods disclosed herein do not depend on additions, deletions, and substitutions of any particular number of nucleotides, it is recognized that such additions, deletions, or substitutions comprises at least one nucleotide.

RNA interference refers to the process of sequence-specific post-transcriptional gene silencing in animals mediated by short interfering RNAs (siRNAs) (Fire et al., *Nature* 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

As used herein, the term "Cas gene" refers to a gene that is generally coupled, associated or close to or in the vicinity of flanking CRISPR loci.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bps, repeated from 1 to 140 times, also referred to as CRISPR-repeats) which are partially palindromic. The repeated sequences (usually specific to a species) are interspaced by variable sequences of constant length (typically 20 to 58 by depending on the CRISPR locus (WO2007/025097, published Mar. 1, 2007).

CRISPR loci were first recognized in *E. coli* (Ishino et al. (1987) *J. Bacterial.* 169:5429-5433; Nakata et al. (1989) *J. Bacterial.* 171:3553-3556). Similar interspersed short sequence repeats have been identified in *Haloferax mediterranei, Streptococcus pyogenes, Anabaena*, and *Mycobacterium tuberculosis* (Groenen et al. (1993) *Mol. Microbiol.* 10:1057-1065; Hoe et al. (1999) *Emerg. Infect. Dis.* 5:254-263; Masepohl et al. (1996) *Biochim. Biophys. Acta* 1307: 26-30; Mojica et al. (1995) *Mol. Microbiol.* 17:85-93). The CRISPR loci differ from other SSRs by the structure of the repeats, which have been termed short regularly spaced repeats (SRSRs) (Janssen et al. (2002) *OMICS J. Integ. Biol.* 6:23-33; Mojica et al. (2000) *Mol. Microbiol.* 36:244-246). The repeats are short elements that occur in clusters, that are always regularly spaced by variable sequences of constant length (Mojica et al. (2000) *Mol. Microbiol.* 36:244-246).

The terms "Cas gene", "CRISPR-associated (Cas) gene" are used interchangeably herein. A comprehensive review of the Cas protein family is presented in Haft et al. (2005) *Computational Biology, PLoS Comput Biol* 1(6): e60. doi: 10.1371/journal.pcbi.0010060. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species. The Cas endonuclease gene can be a Cas9 endonuclease gene, such as but not limited to, Cas9 genes listed in SEQ ID NOs: 462, 474, 489, 494, 499, 505, and 518 of WO2007/025097 published Mar. 1, 2007, and incorporated herein by reference.

As used herein, the term "guide RNA" refers to a synthetic fusion of two RNA molecules, a crRNA (CRISPR RNA) comprising a variable targeting domain, and a tracr-RNA. In one embodiment, the guide RNA comprises a variable targeting domain of 12 to 30 nucleotide sequences and a RNA fragment that can interact with a Cas endonuclease.

The term "variable targeting domain" refers to a nucleotide sequence 5-prime of the GUUUU sequence motif in the guide RNA, that is complementary to one strand of a double strand DNA target site in the genome of a plant cell, plant or seed.

The guide RNA and Cas endonuclease are capable of forming a complex, referred to as "guide RNA/Cas endonuclease complex" or "guide RNA/Cas endonuclease system" that enables the Cas endonuclease to introduce a double strand break at a DNA target site.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

TABLE 1

Summary of SEQ ID NOS

| SEQ ID: | Description |
|---|---|
| 1 | Wheat MS45 promoter_4AL |
| 2 | Wheat MS45 promoter_4BS |
| 3 | Wheat MS45 promoter_4DL |
| 4 | Wheat MS45 promoter consensus |
| 5 | Maize MS45 promoter fragment |
| 6 | Wheat pIR |
| 7 | PHP 54693 T-DNA (5804 bp) |
| 8 | Rice MS45 genomic region used in PHP37034 (2079 bp) |
| 9 | Maize MS45 promoter region used in PHP 37034 (488 bp) |
| 10 | Rice MS26 cds |
| 11 | Plant-optimized DAM (837 bp) |
| 12 | PHP 56791 T-DNA |
| 13 | PHP 54783 T-DNA |
| 14 | Maize/wheat consensus of FIG. 2 |
| 15 | Wheat PRO/pIR consensus of FIG. 3 |
| 16 | Full-length consensus of FIGS. 1A and 1B |
| 17 | PHP 56988 T-DNA |

EXPERIMENTAL

Example 1. Identification of Wheat MS45 Regulatory Region

This example demonstrates the identification of the wheat DNA sequences that correspond to elements to control expression of wheat MS45 in planta.

The 413 amino acid sequence of *Zea mays* MS45 (Cigan et al. (2001) *Sex Plant Reprod.* 14:135-142) was used to search the wheat genomic 454 sequences, CerealsDB, (Wilkenson et al (2012) *BMC Bioinformatics* 13: 219) of Chinese Spring wheat to identify and assembly contigs containing wheat MS45 ortholog sequences. Three non-identical contigs were assembled of approximately 1000 nucleotides, corresponding to sequences from 4AL, 4B S and 4DL corresponding hexaploid wheat *Triticum aestivum* (SEQ ID NOs: 1, 2, and 3). Alignment of theses sequences reveals high sequence identity across the three contigs from wheat (FIG. 1). Similarly, alignment of a 500 bp region containing a consensus sequence of the wheat promoters (SEQ ID NO: 4) with the 500 bp region (SEQ ID NO: 5) containing the ZmMS45 promoter region shows regions of similarity extending to nearly 73% identity across nucleotide positions 369-426 of the wheat and maize sequences, suggesting conservation of regulatory elements between wheat and maize. Overall, 45% sequence identity is observed across the entire 500 base pair region of wheat and maize (FIG. 2).

A synthetic DNA sequence (SEQ ID NO: 6) was generated that contains 98% sequence identity to the wheat Ms45 consensus (FIG. 3). The synthetic wheat Ms45 promoter inverted repeat sequence of SEQ ID NO: 6 was used in gene suppression studies described in examples below.

Example 2. Promoter-Inverted-Repeat Expression Affects Plant Fertility in Wheat

This example demonstrates that the fertility or fertility potential of plants can be altered by expression of promoter inverted repeat molecules (pIR) specific for the promoter of a gene that encodes a protein involved in male fertility pathway.

A promoter inverted repeat construct was generated by linking a ubiquitin promoter to inverted repeats which contained a portion of the wheat MS45 promoter (SEQ ID NO: 6), including a NOS spacer segment between the inverted repeat sequences. Nucleic acid molecules and methods for preparing the vector PHP54693 were as previously described (Cigan et al *Plant Journal* (2005) 43, 929-940). SEQ ID NO: 7 contains the T-DNA sequence for PHP54693. PHP54693 was introduced into wheat Fielder variety by *Agrobacterium*-mediated transformation using methods known in the art and referenced elsewhere herein.

Plants were grown in the greenhouse; transgene copy-number was determined by quantitative polymerase chain reaction (QPCR). Plants were grown to maturity and male fertility phenotype was recorded. Results are shown in Table 2.

TABLE 2

Male Fertility phenotype of transgenic wheat plants containing PHP54693.

| PHP54693 | TOTAL EVENTS | SINGLE OR LOW COPY | MULTI-COPY |
|---|---|---|---|
| MALE STERILE | 36 | 20 | 16 |
| MALE FERTILE | 13 | 8 | 5 |
| | 49 | | |

Suppression was sufficient to cause male-sterility in 73% of events. Both single-copy and multi-copy T-DNA insertion events were male-sterile, at approximately equal frequency, indicating that both single-copy and multi-copy insertion events are effective.

Microscopic examination of anthers from several independent PHP54693 plants revealed that these anthers lacked pollen in contrast to similarly staged anthers from untransformed Fielder plants. In addition, microspores isolated from anthers of male sterile PHP54693 plants were observed to break down after the quartet stage of development. This observation is similar to the stage at which microspores from male sterile maize ms45 mutants are observed to break down. These results demonstrate that a pIR construct directed to wheat MS45 promoter is capable of generating male sterile wheat plants.

It is noted that the pIR of PHP54693 is driven by a constitutive, heterologous promoter, i.e. ZmUBI. This demonstrates that one of skill in the art may select from among a wide range of promoters for use in the suppression construct, including any promoter which provides expression in the tissue wherein the target gene is expressed and in which suppression is desired. In certain embodiments the promoter may drive expression preferentially in one or more male reproductive tissues.

The inverted repeat construct may contain sequences of the targeted promoter that are substantially conserved across multiple different genomes of wheat or other polyploid organisms so as to reduce expression of the associated targeted gene. In addition, sequences which are unique in one or more promoter could be added to the conserved sequences in the inverted repeat construct such that all promoter sequences across all genomes are targeted to reduce expression of the targeted region.

Example 3. Expression of Exogenous MS45 Gene Product Restores Fertility

This example demonstrates that male-sterile plants containing a pIR construct targeting the wheat MS45 promoter (PHP54693 T-DNA, SEQ ID NO: 7) can be restored to male fertility when also containing an exogenous MS45 gene construct.

Constructs were prepared containing an MS45 coding sequence derived from rice (SEQ ID NO: 8) operably linked to a heterologous maize Ms45 promoter (SEQ ID NO: 9). This construct was introduced into wheat Fielder variety by *Agrobacterium*-mediated transformation as described above. Regenerated transformed wheat plants were grown in the greenhouse. All regenerated PHP37034 wheat plants were male fertile.

A wheat plant containing a single-copy PHP37034 TDNA insertion (Male 1) was used as a pollen donor and crossed onto two non-identical male sterile PHP54693 plants (Female 1 and Female 2). Seed was harvested from these crosses, planted, and progeny genotyped for the presence of PHP54693 and PHP37034 TDNA insertions by PCR. Plants containing only PHP54693 or both TDNAs, PHP54693 and PHP37034, were grown to maturity and male fertility phenotype recorded.

As shown in Table 3, Group 1 and 2 wheat plants containing only PHP54693 did not contain pollen and were male sterile (No Seed). In contrast, PHP54693 plants also containing PHP37034 from both groups shed pollen and were capable of self-fertilization (Seed). Seed number per plant in PHP54693/PHP37034 progeny was similar to seed numbers obtained from untransformed Fielder variety plants.

TABLE 3

Male fertility phenotype of transgenic wheat plants containing Dominant sterility construct PHP54693 and Restorer PHP37034.

| PLANT | GROUP | Dominant Sterility Construct PHP54693 | RESTORER PHP37034 | FEMALE | MALE | SEED SET |
|---|---|---|---|---|---|---|
| 1 | 1 | + | + | 1 | 1 | SEED |
| 2 | 1 | + | + | 1 | 1 | SEED |
| 3 | 1 | + | + | 1 | 1 | SEED |
| 4 | 1 | + |   | 1 | 1 | NO SEED |
| 5 | 1 | + |   | 1 | 1 | NO SEED |
| 6 | 1 | + |   | 1 | 1 | NO SEED |
| 1 | 2 | + | + | 2 | 1 | SEED |
| 2 | 2 | + | + | 2 | 1 | SEED |
| 3 | 2 | + | + | 2 | 1 | SEED |
| 4 | 2 | + | + | 2 | 1 | SEED |
| 5 | 2 | + |   | 2 | 1 | NO SEED |
| 6 | 2 | + |   | 2 | 1 | NO SEED |

These data provide the surprising result that in hexaploid Fielder wheat, the A, B and D genome copies of the wheat Ms45 promoter are suppressed by PHP54693, resulting in the loss or reduction of Ms45 expression sufficient to confer wheat male sterile. These results further demonstrate that an exogenous MS45 gene construct contained in PHP37034 is capable of restoring fertility to hexaploid wheat plants containing the Dominant male sterility construct PHP54693 which suppresses the endogenous wheat MS45 gene.

Example 4. Use of Exogenous MS45 Gene Products to Restore Fertility in PHP54693 Plants The promoter expressing the rice MS45 gene in PHP37034 can be derived from a source other than maize; for example, the rice and *Arabidopsis* homologs of the maize MS45, 5126, BS7 and MS26 genes, can be used, or any plant promoter capable of transcribing MS45 such that expression of the transcription unit renders plants male fertile, including a constitutive promoter. In certain respects, it is advantageous to use non-wheat promoters to express the fertility-restoring gene, such as the MS45 gene. For example, where promoter inverted repeats from the same species reduce target gene function such that the plant is non-viable or non-reproductive, a promoter from a different species can be used to transcriptionally express the complementing gene function (e.g., MS45), thus circumventing this potential problem. Alternatively, promoters natively associated with genes other than MS45 may be used, provided that the expression occurs at least in tissues in which complementation is desired, including male-tissue-preferred or constitutive promoters from wheat or from other species. Further, a native promoter, for example a wheat MS45 promoter, can be used to drive the fertility-restoring gene if that native promoter is sufficiently altered that it is not targeted by the pIR.

In addition, the MS45 gene in PHP37034 can be from a source other than rice, for example the maize or wheat MS45 coding region or other plant sources of an Ms45 gene or like gene capable of complementing the Ms45 function and restoring male fertility.

Taken together, the present Examples demonstrate that an endogenous polyploid plant fertility gene can be inactivated using promoter inverted repeat-mediated suppression, and that a fertile phenotype can be restored in genotypically sterile plants.

Example 5. Inbred Maintenance and Increase of LOF-pIRmf Male Sterile Plants Using a Hemizygous Maintainer It would be advantageous to produce a pure line of male sterile plants to allow for cross pollination with a different inbred variety to produce hybrid seed. Generally, strategies that incorporate dominant sterility as a means to invoke male sterility cannot self-pollinate. This example provides such a method.

Figure 5:
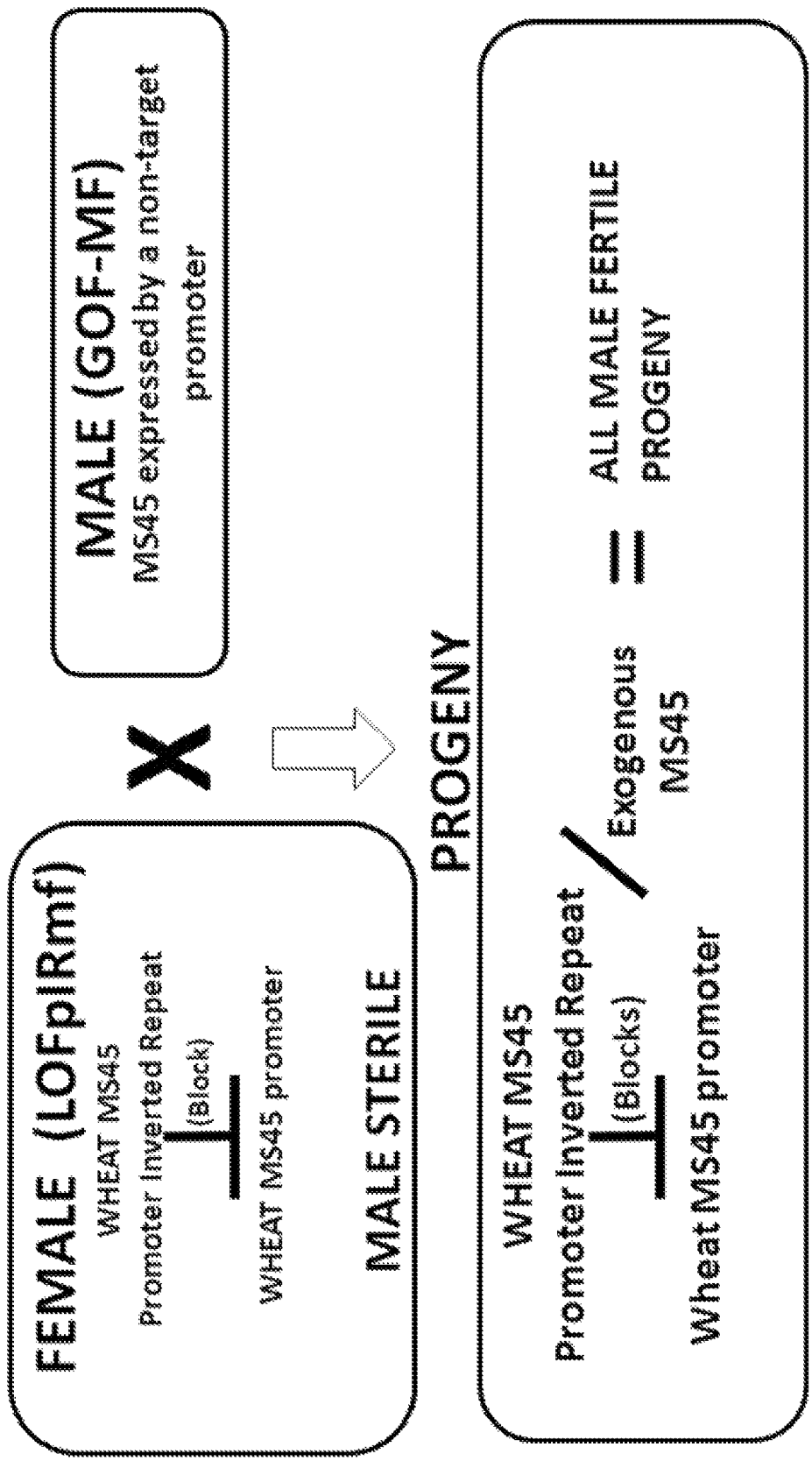
FIG. 5. Restoration of fertility by Gain of Function: GOF-MF; MS45.

In some embodiments, when promoter inverted repeat strategies are used to silence genes involved in male fertility (Loss of Function: LOF-pIRmf), supplying an exogenous copy of the silenced gene restores male fertility. This is an example of restoration of fertility by Gain of Function (GOF-MF) (FIG. 4). As described previously, when silencing the wheat MS45 gene and restoring using an exogenous source of the suppressed fertility gene, the female inbreds are examples of LOF-pIRmf, while the male restorers are examples of GOF-MF (FIG. 5).

It would be advantageous to generate an inbred maintainer population, to increase the male sterile inbred line. To accomplish this, in one embodiment for wheat, the maize MS45 promoter expressing the rice MS45 gene (GOF-MF) is linked to the maize alpha amylase gene under control of the maize PG47 promoter and linked to a DsRed2 gene under control of the barley LTP2 promoter (see, e.g., U.S. Pat. No. 5,525,716) and also carrying a PINII terminator sequence (GOF-MF-AA-DsRED). This construct is transformed directly into wheat by *Agrobacterium*-mediated transformation. Wheat plants containing single-copy GOF-MF-AA-DsRED cassette are emasculated and stigmas are fertilized with pollen from male fertile plants containing LOF-pIRmf and GOF-MF constructs. Seeds are harvested, screening by PCR for plants or seeds containing only the GOF-MF-AA-DsRED and LOF-pIRmf TDNA insertions. These seeds are planted and plants are allowed to self-pollinate. Red fluorescing seed from these selfed plants are planted and progeny screened by QPCR for homozygous LOF-pIRmf TDNA insertions. Seed from this generation of progeny segregates at a frequency of 1:1 red and non-red fluorescing. Red-fluorescing seed is hemizygous for GOF-MF-AA-DsRED, homozygous for LOF-pIRmf, while non-fluorescing seed is homozygous for LOF-pIRmf. Progeny of the non-fluorescing seed are male sterile and can be used as female inbreds during hybrid production. The red-fluorescing seed produce progeny (hemizygous for GOF-MF-AA-DsRED;homozygous LOF-pIRmf) that can be used to maintain and propagate the male sterile inbred.

Example 6. *E. coli* DNA (Adenosine-N6-)-Methyltransferase (DAM) Expression Affects Plant Fertility in Wheat This example demonstrates that the fertility or fertility potential of wheat plants can be altered by expression of *E. coli* DNA (Adenosine-N6-)-Methyltransferase (DAM) when under the control of the maize anther promoter 5126.

In maize, anther-directed expression of the *E. coli* DAM gene resulted in a high frequency of male sterile plants due to disruption of normal tapetum function (Unger et al (2001) Trans Res 10: 409-422). However, it was not known whether expression of DAM in a polyploid plant would result in male sterility.

Nucleic acid molecules and methods for preparing a vector to express in wheat plants, PHP56791, are similar to those previously described (Unger et al (2001) Trans Res 10:

409-422). DNA sequence of the DAM gene was modified for expression in plants (SEQ ID NO: 11). The optimized DAM gene was placed under the transcriptional control of the maize 5126 promoter (Unger et al (2001) Trans Res 10: 409-422) to generate the plant transformation vector PHP56791. (SEQ ID NO: 12) PHP56791 was introduced into wheat Fielder variety by *Agrobacterium*-mediated transformation methods similar to those described or referenced elsewhere herein.

Plants were grown in the greenhouse and transgene copy-number was determined by quantitative polymerase chain reaction (QPCR). Plants were grown to maturity and male fertility phenotype was recorded. As shown in Table 4, of the 85 primary T0 wheat transformants, 73 plants were male sterile while 12 plants were male fertile. Microscopic examination of anthers from several independent PHP56791 plants revealed that these anthers lacked pollen in contrast to similarly staged anthers from untransformed Fielder plants. In addition, anthers were consistently one-third to one-half the size of fully-developed fertile anthers and did not contain microspores beyond the early vacuolate stage of development. The small size of the anthers and lack of pollen in PHP56791 male sterile plants were similar to the male sterility phenotypes observed in maize plants transformed with anther-expressed DAM gene.

These results demonstrate that the plant optimized DAM gene expressed from the maize anther promoter in PHP56791 is capable of generating male sterile wheat plants.

TABLE 4

Frequency of male sterility in plants containing PHP56791

| PHP56791 | TOTAL EVENTS | SINGLE OR LOW COPY | MULTI-COPY |
|---|---|---|---|
| MALE STERILE | 73 | 46 | 27 |
| MALE FERTILE | 12 | 8 | 4 |
| | 85 | | |

Example 7. Preparation of Wheat Male Sterility Restorer Lines and Restoration of Male Fertility to PHP56791 Containing Wheat Plants This example demonstrates that male-sterile plants containing construct PHP56791 can be restored to male fertility when also containing a promoter silencing construct.

In maize, promoter silencing constructs effectively transcriptionally silence both endogenous and transformed promoters in planta (Cigan et al *Plant Journal* (2005) 43, 929-940). This example was designed to test whether a promoter inverted repeat designed to silence the maize anther promoter, 5126, was capable of directing similar male sterility phenotypes in wheat. In addition, if fertility was not impacted by the maize 5126 promoter inverted repeat, the experiment would determine whether this silencing cassette could suppress the anther expression of the DAM gene in PHP56791 transgenic wheat plants.

Nucleic acid molecules and methods for preparing the plant vector PHP54783 capable of suppressing the maize 5126 promoter used to express the DAM gene in PHP56791 are essentially as described for PHP20089 (Cigan et al *Plant Journal* (2005) 43, 929-940). PHP54783 (SEQ ID NO: 13) was introduced into wheat Fielder variety by *Agrobacterium*-mediated transformation methods similar to those described or referenced elsewhere herein. Transformed plants were regenerated from tissue culture and grown in the greenhouse. Transgene copy-number was determined by quantitative polymerase chain reaction (QPCR). Plants were grown to maturity and male fertility phenotype was recorded.

All plants containing only the PHP54783 TDNA insertions were male fertile, suggesting that unlike expression of this pIR suppression cassette in maize, the Zm5126 pIR does not result in male sterile wheat plants.

To determine whether the Zm5126 pIR silencing cassette was capable of reversing the male sterility phenotype associated with PHP56791, pollen from two non-identical single-copy PHP54783 TDNA insertions (Male 1 and Male 2) were used to fertilize three non-identical, male sterile, PHP56791 plants (Female 1, 3, 4). Seed was harvested from these crosses, planted and progeny genotyped for the presence of PHP54783 and PHP56791 TDNA insertions by PCR. Plants containing only PHP56791, or both PHP56791 and PHP54783, were grown to maturity and male fertility phenotype recorded. As shown in Table 5, Group 1 and 4 wheat plants containing only PHP56791 did not contain pollen and were male sterile (No Seed).

TABLE 5

Male Fertility phenotype of transgenic wheat plants containing Dominant sterility construct PHP56791 and Restorer PHP54783.

| PLANT | GROUP | Dominant Sterility Construct PHP56791 | RESTORER PHP54783 | FEMALE | MALE | SEED SET |
|---|---|---|---|---|---|---|
| 1 | 1 | + | + | 1 | 1 | SEED |
| 2 | 1 | + |   | 1 | 1 | NO SEED |
| 3 | 1 | + |   | 1 | 1 | NO SEED |
| 4 | 1 | + |   | 1 | 1 | NO SEED |
| 1 | 3 | + | + | 3 | 1 | SEED |
| 1 | 4 | + | + | 4 | 2 | SEED |
| 2 | 4 | + | + | 4 | 2 | SEED |
| 3 | 4 | + | + | 4 | 2 | SEED |
| 4 | 4 | + |   | 4 | 2 | NO SEED |
| 5 | 4 | + |   | 4 | 2 | NO SEED |
| 6 | 4 | + |   | 4 | 2 | NO SEED |

In contrast, PHP56791 plants also containing PHP54783 from Groups 1, 3 and 4 shed pollen and were capable of self-fertilization (Seed). Seed number per plant in PHP56791/PHP54783 progeny was similar to seed numbers obtained from untransformed Fielder variety plants. These results demonstrate that the *Zea mays* 5126 promoter inverted repeat was capable of restoring fertility to wheat plants containing the Dominant male sterility construct PHP56791.

Example 8. Sources of Promoters and Gene Products to Confer Male Sterility and Restore Fertility in Wheat The promoter expressing the *E. coli* DAM gene in PHP56791 can be an anther-preferred promoter such as the promoter of the maize MS45, BS7 or MS26 gene, or for example, the promoter of the rice or *Arabidopsis* homolog of the maize MS45, 5126, BS7 or MS26 gene, such that expression by this plant promoter: DAM transcription unit renders wheat plants male sterile. In certain respects, it is advantageous to use non-wheat promoters to express the DAM gene. For example, where promoter inverted repeats from the same species have the potential to reduce target promoter function such that the plant is non-viable or non-reproductive, a promoter from a different species can be used to transcriptionally express the dominant sterility gene (e.g., DAM), thus circumventing this potential problem.

In addition, the *E. coli* DAM gene in PHP56791 can be replaced by sources other than DAM, for example barnase or another gene product that renders plants male sterile as a result of reduced tapetum function or other disruption of development of male reproductive tissue.

Taken together, the present Examples demonstrate that a Dominant male sterility gene can be inactivated using pIR-mediated suppression, and that a fertile phenotype can be restored in genotypically sterile plants.

Example 9. Inbred Maintenance and Increase of LOF-DomMS Male Sterile Plants Using a Hemizygous Maintainer It would be advantageous to produce a pure line of male sterile plants to allow for cross pollination with a different inbred variety to produce hybrid seed. Generally, sterility strategies that include dominant approaches prevent plants from self-pollinating. This example provides such a method.

Figure 6:
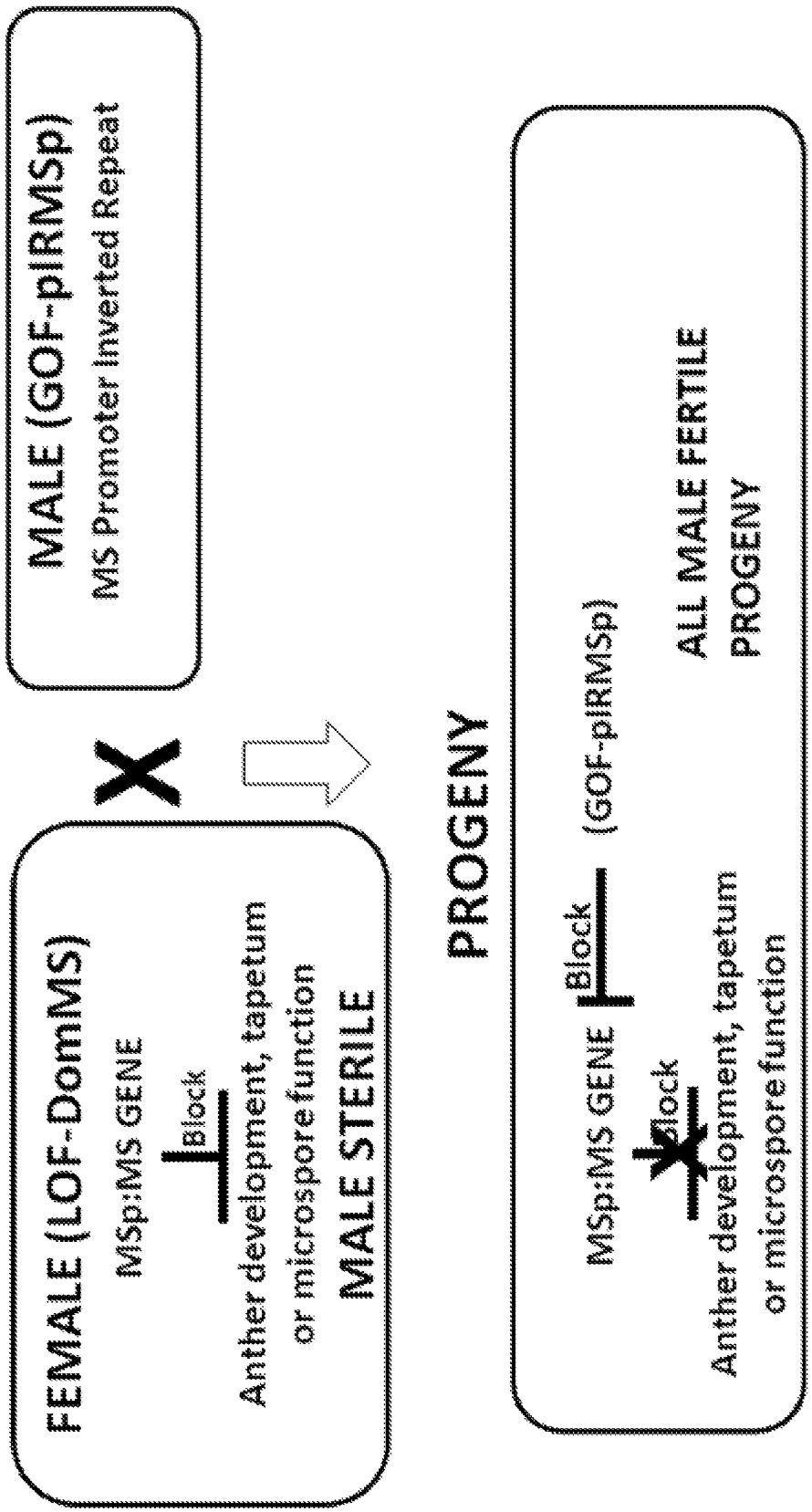
FIG. 6. Restoration of fertility by Gain of Function: GOF-pIRMSp.
Figure 7:
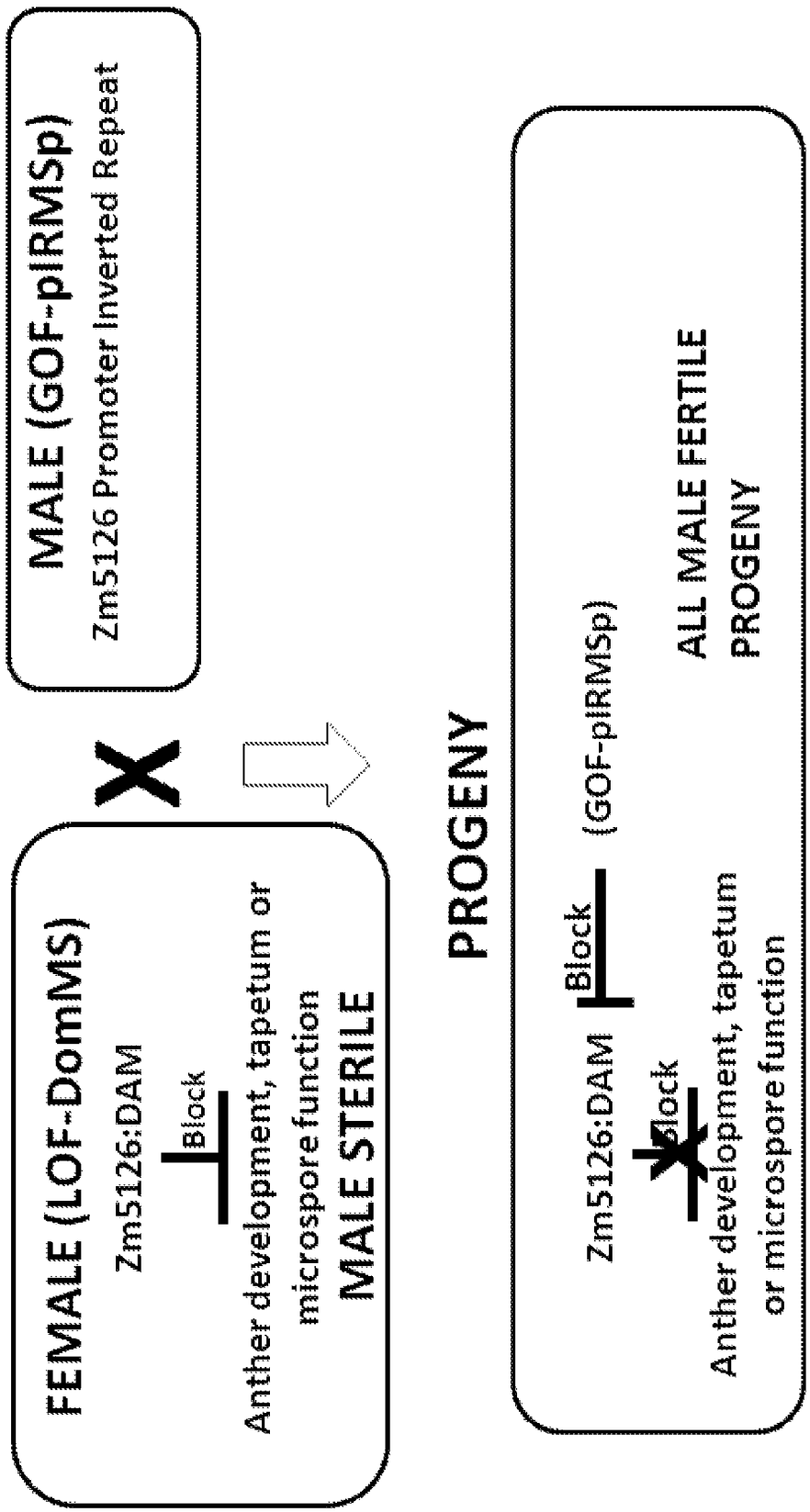
FIG. 7. Restoration of fertility by Gain of Function: GOF-pIRMSp; 5126:DAM.

In some embodiments, dominant male sterility is accomplished by the introduction of a construct comprising a promoter driving a gene to express a gene product, such as a protein or RNA, that causes male sterile plants due to general or specific disruption of reproductive development, such as anther development, tapetum development or microspore function. In these Dominant Loss of Function (LOF-DomMS) examples, restoration of fertility could be accomplished by co-expressing an exogenous promoter inverted repeat (pIR) construct that silences the promoter (MSp) used to drive the Dominant sterility gene (MSpMS). This is an example of restoration of fertility by Gain of Function by promoter inverted repeats (GOF-pIRMSp) (FIG. 6). As described previously, disrupting normal tapetum function by Zm5126:DAM (MSpMS) is an example of the LOF-DomMS female inbred; restoration of fertility using an exogenous source of the Zm5126pIR (pIRMSp) is an example of GOF-pIRMSp (FIG. 7).

It would be advantageous to generate an inbred maintainer population which could be used to increase the male sterile inbred line containing MSpMS. To accomplish this, the GOF-pIRMSp is linked to the maize alpha amylase gene under control of the PG47 promoter and linked to a DsRed2 gene under control of the barley LTP2 promoter (see, e.g., U.S. Pat. No. 5,525,716) and also carrying a PINII terminator sequence (GOF-pIRMSp-AA-DsRED). This construct is transformed directly into wheat by *Agrobacterium*-mediated transformation. Wheat plants containing single-copy GOF-pIRMSp-AA-DsRED cassette are emasculated and stigmas are fertilized with pollen from male fertile plants containing MSpMS/GOF-pIRMSp. Seeds are harvested, screening by PCR for plants or seeds containing only the GOF-pIRMSp-AA-DsRED and MSpMS TDNA insertions. Plants are allowed to self-pollinate. Red fluorescing seed from these selfed plants are planted and progeny screened by QPCR for homozygous MSpMS TDNA insertions. Seed from this generation of progeny will segregate at a frequency of 1:1 red and non-red fluorescing. Red fluorescing seed is hemizygous for GOF-pIRMSp-AA-DsRED and homozygous for MSpMS; while non-fluorescing seed is homozygous for MSpMS. Progeny of the non-fluorescing seed are male sterile and can be used as female inbreds during hybrid production. The red fluorescing seed produce progeny (hemizygous for GOF-pIRMSp-AA-DsRED; homozygous for MSpMS) that would be used to propagate the male sterile inbred. In the example above, the MSpMS could be Zm5126DAM, while GOF-pIRMSp would correspond to Zm5126pIR.

As the progeny produced during hybrid seed production would contain a hemizygous dominant sterility-causing gene construct, MSpMS, it would be advantageous to generate male inbred varieties that contain homozygous male fertility restorer (GOF-pIRMSp). It could be envisioned that these male inbred varieties would be used during hybrid production. F1 seed, generated by fertilization of MSpMS/MSpMS male sterile females with pollen from male fertile pIRMSp/pIRMSp male inbreds, would be genotypically MSpMS/pIRMSp and phenotypically male fertile.

Example 10. Maintenance of Male Sterile Inbreds Containing LOF-pIRmf and GOF-MF-AA-DsRED In this example, fertility was restored to wheat plants containing a pIR construct targeting the wheat MS45 promoter (PHP54693 T-DNA;TaMS45pIR) using a functional copy of the maize MS45 gene linked to (a) the maize alpha amylase gene under control of the PG47 promoter and (b) a DsRed2 gene under control of the barley LTP2 promoter (see, e.g., U.S. Pat. No. 5,525,716), GOF-MF-AA-DsRED.

It would be advantageous to produce a pure line of male sterile plants to allow for cross pollination with a different inbred variety to produce hybrid seed. Wheat plants containing PHP56988 (T-DNA comprising a maize MS45 gene linked to the pollen PG47 promoter expressing maize alpha amylase and a third gene composed of the barley LTP2 promoter expressing the fluorescent marker, DsRed2; SEQ ID NO: 17) were used to maintain male fertility. This maintainer line construct, PHP56988, was initially generated by *Agrobacterium*-mediated transformation. Pollen from TaMS45pIR plants containing the MS45 restorer (Example 4) was then used to fertilize emasculated wheat plants containing PHP56988. Seeds were harvested, and progeny plants were screened by PCR to select those containing only GOF-MF-AA-DsRED (PHP56988) and LOF-pIRmf TDNA (PHP54693) insertions. Plants were allowed to self-pollinate. Red fluorescing seed (indicating inheritance of the DsRed marker in PHP56988) from these selfed plants was planted and progeny screened by QPCR for homozygous LOFpIRmf (PHP54693); seed from this generation of progeny segregates at a frequency of 1:1 red and non-red fluorescing. Red-fluorescing seed was hemizygous (one copy) for GOF-MF-AA-DsRED (PHP56988) and homozygous (two copies) for LOF-pIRmf (PHP54693), while non-fluorescing seed were homozygous for LOF-pIRmf (PHP54693). Progeny of the non-fluorescing seed were male sterile due to the presence of the LOF-pIRmf TDNA insert. The red-fluorescing seed progeny (hemizygous for GOF-MF-AA-DsRED;homozygous LOF-pIRmf) were male fertile and set seed.

This example demonstrates that the male sterility phenotype conferred by the promoter inverted repeat directed against the wheat MS45 promoter carried in LOF-pIRmf vector PHP54693, could be reversed by the presence and action of the functional Ms45 copy contained in the GOF-MF-AA-DsRED. In addition, 1:1 segregation of male fertility phenotype with male sterile phenotype was coincident with the presence of PHP56988 (GOF-MF-AA-DsRED) and PHP54693 (LOF-pIRmf) or PHP54693 (LOF-pIRmf) only, respectively.

Example 11. Restoration of Male Fertility in Hybrid Plants Containing LOF-pIRmf The pure line of LOF-pIRmf male sterile plants used as females and cross-pollinated with a different male inbred variety would produce hybrid seed in which the LOF-pIRmf insertions would be hemizygous. The progeny plants derived from this F1 seed would be male sterile and incapable of producing pollen and selfed seed. It would be advantageous to devise strategies that allow for the self-fertilization of the hybrid seed containing hemizygous LOF-pIRmf insertions. In these examples, various strategies to overcome the sterility imparted by LOF-pIRmf in F1 hybrids are described.

One solution to overcome F1 sterility would be to use a male inbred variety which contains a copy of Ms45 or the pIR targeted fertility gene which is not silenced by the TaMS45pIR or LOF-pIRmf, respectively. This solution was described in Example 3 where PHP37034-containing wheat plants restored fertility when crossed onto homozygous or hemizygous TaMs45pIR containing plants. Thus, male inbred varieties could contain homozygous PHP37034 or similar restoring constructs, and used as pollen donors during hybrid seed production. All F1 hybrid seed would produce fertile plants, as the hemizygous copy of exogenously supplied Ms45 would restore function by complementing the wheat Ms45 gene which was silenced by the action of the TaMs45pIR.

A second solution to restore fertility in the F1 plant would be to use a male inbred variety which contains a genic modified copy of the wheat Ms45 or the pIR-targeted fertility gene promoter which is not silenced by the TaMS45pIR or LOF-pIRmf, respectively. In this example, the endogenous wheat Ms45 promoter could be replaced with DNA sequences which would not be targeted for silencing by the TaMs45pIR yet would be competent for expressing a fertility complementing version of wheat Ms45. The plant genome could be manipulated using DNA cutting reagents (for example, Zinc Finger nucleases, TALE nucleases, custom meganuclease or guide RNA/Cas endonuclease systems) to introduce a double-strand-break in the region of the endogenous native wheat Ms45 gene and an exogenously supplied DNA template which contains promoter sequences sufficient to express wheat Ms45 but not targeted for silencing by the TaMs45pIR (maize or rice Ms45 or 5126 for example, or a combination of wheat and non-wheat derived sequences). By producing a double-strand-break in this region which promotes homologous recombination, the wheat Ms45 promoter could be replaced or altered to the extent that the region is no longer a target for suppression or silencing. Male inbreds that contain this non-target promoter at the fertility locus would be used as pollen donors during hybrid seed production. All F1 seed would produce male fertile plants, as the hemizygous copy of the endogenous TaMs45 gene now linked to a non-target promoter is not silenced by the action of TaMs45pIR also present in these progeny.

Another solution that could be devised to restore fertility in the F1 plant would be to design promoter inverted repeats that function only as a paired system (LOF-pIR1mf/LOF-pIR2mf) but do not function when present only in a hemizygous unpaired state. The constitutively expressed promoter inverted repeat RNA is processed by the dicer enzyme DCL3 to 24 nt siRNAs which are initially bound to AGO4. The AGO4-siRNAs duplex directs a silencing complex to homologous genomic regions through basepairing to DNA. As the generation of these 24 nt small RNAs is independent of the source of the constitutively expressed promoter inverted repeat RNA, it could be envisioned that multiple promoter inverted repeat constructs could be designed to generate sufficient 24nt small RNA coverage of the targeted promoter region. In this example female inbreds containing hemizygous promoter inverted repeats would be fertilized with any wild-type male inbred variety. The hemizygous unpaired promoter inverted repeat containing progeny would be male fertile due to the inability of a single promoter inverted repeat to silence the fertility target promoter. Promoter inverted repeat pairs could be designed such that the first promoter inverted repeat construct would contain only part of the target sequence, while the second promoter inverted repeat could contain the remaining portion of the target promoter needed for silencing. As the promoter being targeted would not be silenced or suppressed due to incomplete coverage by a single promoter inverted repeat, only in the presence of the paired first and second promoter inverted repeat would the target promoter be silenced. Plants, generated to contain the unique pairs of promoter inverted repeat constructs at a single location in the plant genome, would be crossed to generate a male sterile female inbred line due to the silencing of the fertility gene by the combined action of the paired promoter inverted repeats. This female inbred line would be maintained by a GOF-MF-AA-DsRED construct which would allow for the generation of a segregating population: one half of the seed population would fluoresce due to the presence of GOF-MF-AA-DsRED and hemizygous LOF-pIR1mf/LOF-pIR2mf, while the other half of the seed population would not fluoresce but only contain hemizygous LOF-pIR1mf/LOF-pIR2mf. Progeny containing GOF-MF-AA-DsRED and hemizygous LOF-pIR1mf/LOE-pIR2mf would be male fertile, while progeny LOF-pIR1mf/LOF-pIR2mf plants would be male sterile and used as female inbreds during hybrid production. Fertilization of LOF-pIR1mf/LOF-pIR2mf plants with wild-type male inbred would result in progeny which would segregate away each copy of LOF-pIR1mf and LOF-pIR2mf insertions, yielding LOF-pIR1mf-only and LOF-pIR2mf-only plants which would be male fertile, as these single LOF-pIRmf versions are incapable of silencing the endogenous copies of the fertility gene. It could be envisioned that multiple promoter inverted repeat combinations could be designed to enable silencing of the target promoter; these could include, but are not limited to, promoter inverted repeat pairs that contain contiguous stretches of DNA sequence, splitting DNA sequences equally or unequally, the target promoter sequence, or chimeras consisting of stretches of non-contiguous, overlapping or non-overlapping, DNA target sequences. Moreover, it could be envisioned that the order of these sequences within these paired promoter inverted repeat constructs could be altered and different relative to order of the target DNA sequence.

That which is claimed:

1. An isolated nucleic acid molecule comprising a polynucleotide selected from the group consisting of:
   (a) a nucleotide sequence comprising the nucleotide sequence of SEQ ID NO: 1, 2 or 3;
   (b) a nucleotide sequence from a wheat Ms45 gene and comprising a fragment of the nucleotide sequence of SEQ ID NO: 1, 2, or 3, wherein the fragment is at least 500 nucleotides long and has at least 90% sequence identity to the nucleotide sequence of SEQ ID NO:4, and wherein the fragment-initiates transcription in a plant cell; and
   (c) a polynucleotide which is complementary to the full length polynucleotide of (a) or (b);
   wherein the polynucleotide of (a), (b), or (c) is operably linked to a heterologous polynucleotide of interest.

2. An expression cassette comprising the polynucleotide of claim 1.

3. A vector comprising the expression cassette of claim 2.

4. A plant cell comprising the expression cassette of claim 2.

5. The plant cell of claim 4, wherein said expression cassette is stably integrated into the genome of the plant cell.

6. The plant cell of claim 4, wherein said plant cell is from a monocot.

7. The plant cell of claim 6, wherein said monocot is wheat or maize.

8. A plant comprising the expression cassette of claim 2.

9. The plant of claim 8, wherein said plant is a monocot.

10. The plant of claim 9, wherein said monocot is wheat or maize.

11. The plant of claim 8, wherein said expression cassette is stably incorporated into the genome of the plant.

12. A transgenic seed of the plant of claim 11, wherein the seed comprises the expression cassette.

13. The plant of claim 8, wherein the heterologous polynucleotide of interest encodes a gene product that confers drought tolerance, cold tolerance, herbicide tolerance, pathogen resistance, or insect resistance, or impacts fertility of the plant.

14. The plant of claim 8, wherein expression of said polynucleotide alters the phenotype of said plant.

15. A method for expressing a polynucleotide in a plant or a plant cell, said method comprising introducing into the plant or the plant cell a promoter operably linked to a polynucleotide of interest, wherein said promoter is heterologous with respect to the plant or plant cell, and wherein said promoter comprises a nucleotide sequence selected from the group consisting of:
   (a) a nucleotide sequence comprising the nucleotide sequence of SEQ ID NO: 1, 2 or 3;
   (b) a nucleotide sequence from a wheat Ms45 gene and comprising a fragment of the nucleotide sequence of SEQ ID NO: 1, 2, or 3, wherein the fragment is at least 500 nucleotides long and has at least 90% sequence identity to the nucleotide sequence of SEQ ID NO:4, and wherein the fragment-initiates transcription in a plant cell; and
   (c) a nucleotide sequence which is complementary to the full length nucleotide sequence of (a) or (b).

16. The method of claim 15, wherein the polynucleotide of interest encodes a gene product that impacts fertility of the plant.

17. The method of claim 15, wherein said plant is a monocot.

18. The method of claim 17, wherein said monocot is maize or wheat.

19. A method for expressing a polynucleotide preferentially in male reproductive tissues of a plant, said method comprising introducing into a plant cell an expression cassette and regenerating a plant from said plant cell, said plant having stably incorporated into its genome the expression cassette, said expression cassette comprising a promoter operably linked to a heterologous polynucleotide of interest, wherein said promoter comprises a nucleotide sequence selected from the group consisting of:
   (a) a nucleotide sequence comprising the nucleotide sequence of SEQ ID NO: 1, 2 or 3;
   (b) a nucleotide sequence from a wheat Ms45 gene and comprising a fragment of the nucleotide sequence of SEQ ID NO: 1, 2, or 3, wherein the fragment is at least 500 nucleotides long and has at least 90% sequence identity to the nucleotide sequence of SEQ ID NO:4, and wherein the fragment-initiates transcription in a plant cell; and
   (c) a nucleotide sequence which is complementary to the full length nucleotide sequence of (a) or (b).

20. The method of claim 19, wherein the heterologous polynucleotide of interest encodes a gene product that confers drought tolerance, cold tolerance, herbicide tolerance, pathogen resistance, or insect resistance, or impacts fertility of the plant.

21. The method of claim 19, wherein said plant is a monocot.

22. The method of claim 21, wherein said monocot is wheat or maize.

* * * * *